(12) United States Patent
Zhu (10) Patent No.: US 8,034,330 B2
(45) Date of Patent: Oct. 11, 2011

(54) MODIFIED ORGANS AND CELLS FOR XENOTRANSPLANTATION

(75) Inventor: Alex Zhu, New York, NY (US)

(73) Assignee: RBC Biotechnology, Inc., New York, NY (US)

( * ) Notice: Subject to any disclaimer, the term of this patent is extended or adjusted under 35 U.S.C. 154(b) by 627 days.

(21) Appl. No.: 11/561,470

(22) Filed: Nov. 20, 2006

(65) Prior Publication Data

US 2007/0089178 A1    Apr. 19, 2007

Related U.S. Application Data

(62) Division of application No. 10/135,919, filed on Apr. 29, 2002, now Pat. No. 7,166,278.

(60) Provisional application No. 60/287,684, filed on Apr. 30, 2001, provisional application No. 60/300,604, filed on Jun. 22, 2001, provisional application No. 60/333,876, filed on Nov. 28, 2001.

(51) Int. Cl.
*A61K 35/12* (2006.01)
*C12N 5/07* (2010.01)
*C12N 5/10* (2006.01)
*A01K 67/00* (2006.01)

(52) U.S. Cl. .......... 424/93.2; 435/325; 435/1.1; 800/17; 800/21

(58) Field of Classification Search ............... 435/325, 435/1.1; 800/17, 21; 424/93.2
See application file for complete search history.

(56) References Cited

U.S. PATENT DOCUMENTS

| 6,166,288 | A | * | 12/2000 | Diamond et al. | ............... 800/17 |
| 6,228,631 | B1 | | 5/2001 | Zhu et al. | |
| 6,245,890 | B1 | | 6/2001 | Zhu et al. | |
| 6,331,658 | B1 | | 12/2001 | Cooper et al. | |

FOREIGN PATENT DOCUMENTS

| EP | 0 517 916 | 12/1992 |
| WO | WO 92/17189 | 10/1992 |
| WO | WO 95/20661 | 8/1995 |
| WO | WO 97/12035 | 4/1997 |

OTHER PUBLICATIONS

Bouhours et al. (1996) Glycoconj. J., vol. 13, 947-953.*
Fontana et al. (1999) Animal Cell Technology: Products from Cells, Cells as Products-Proceedings of the 16th ESACT Meeting, Apr. 25-29, 1999, Lugano, Switzerland, 245-247, and 249.*
Irie, et al., "The molecular basis for the absence of N-glycolylneuraminic acid in humans", J. Biol. Chem., 273(25):15866-15871 (1998).
Okajima, "Molecular cloning of a novel alpha2,3-sialyltransferase (ST3Gal VI) that sialylates type II lactosamine structures on glycoproteins and glycolipids", J. Biol. Chem., 274(17):11479-11486 (1999).
Hamanaka, et al., "Occurrence of hematoside with two moles of N-acetyl-neuraminic acid in a certain breed of Persian cat", J. Biochem., 86:695-698 (1979).
Hashimoto, et al., "Further studies on the red cell glycolipids of various breeds of dogs. A possible assumption about the origin of Japanese dogs", J. Biochem., 96:1777-1782 (1984).
Alwayn, et al., "The problem of anti-pig antibodies in pig-to-primate xenografting: current and novel methods of depletion and/or suppression of production of anti-pig antibodies," Xenotransplantation. 6(3):157-168 (1999).
Asaoka, et al., "Detection of N-glycolylneuraminic acid-containing glycoproteins from various animal erythrocytes by chicken monoclonal antibody against Hanganutziu-Deicher antigens," J Vet Med Sci 56(2):375-377 (1994).
Backer, et al., "Biochemical and enzymatic characterization of blood group ABH and related histo-blood group glycosphingolipids in the epithelial cells of porcine small intestine," Glycobiology 7(7): 943-953 (1997).
Bouhours, et al., "A novel glycosphingolipid expressed in pig kidney: Gal alpha 1-3Lewis(x) hexaglycosylceramide," Glycoconj. J. 14(1): 29-38 (1997).
Bouhours, et al., "Simultaneous expression by porcine aorta endothelial cells of glycosphingolipids bearing the major epitope for human xenoreactive antibodies (Gal alpha 1-3Gal), blood group H determinant and N-glycolylneuraminic acid," Glycoconj J 13(6): 947-953 (1996).
Brinkman-Van Der Linden, et al., "Loss of N-glycolyIneuraminic acid in human evolution. Implications for sialic acid recognition by siglecs," J. Biol.Chem. 275(12): 8633-8640 (2000).
Buhler, et al., "High-dose porcine hematopoietic cell transplantation combined with CD40 ligand blockade in baboons prevents an induced anti-pig humoral response," Transplantation 69(11) 2296-2304 (2000). Buhler, et al., "Miniature swine and hDAF pig kidney transplantation in baboons treated with a nonmyeloablative regimen and CD154 blockade," Transplant. Proc. 33(1-2):716 (2001).
Buhler, et al., "Xenotransplantation—state of the art—update 1999," Front Biosci 4: d416-432 (1999).
Cairns, et al., "Thomsen-Friedenreich and PK antigens in pig-to-human xenotransplantation," Transplant. Proc. 28(2):795-796 (1996).
Chou, et al., "A mutation in human CMP-sialic acid hydroxylase occurred after the Homo-Pan divergence," Proc. Natl. Acad. Sci. U S A. 95(20):11751-11756 (1998).
Colman, et al., "Therapeutic cloning: concepts and practicalities," Trends Biotechnol 18(5):192-196 (2000).
Cooper, "Depletion of natural antibodies in non-human primates—a step towards successful discordant xenografting in humans," Clin. Transplant 6(3 Pt 1):178-183 (1992).

(Continued)

Primary Examiner — Anne Marie S Wehbe
(74) Attorney, Agent, or Firm — Pabst Patent Group LLP (57) ABSTRACT

It has been discovered that there are at least two significant antigens present on the cells of animal species such as pigs that elicit an immune or inflammatory response immediately upon implantation into humans or contact with human serum. The first is an α-galactosyl (Gal) epitope, for example, Galα (1→3)Galβ(1→4)GlcNac (linear B type 2) or Galα (1→3)Galβ(1→4)Glc (linear B type 6). The second is an N-glycolylneuraminic acid (NeuGc) structure. By eliminating these epitopes, preferably by genetically engineering the animal so that the epitope is either not produced or is greatly reduced, or by chemical or enzymatic treatment of the animal's cells to remove the epitopes, it is possible to produce organs, tissues and cells suitable for xenotransplantation into humans. Cells can be rendered even more compatible by genetically engineering the animal to express a human complement regulatory protein (inhibitor), such as CD59, on its cells, or to express an excess of a pig complement regulatory protein.

10 Claims, 2 Drawing Sheets

OTHER PUBLICATIONS

Cooper, "Xenoantigens and xenoantibodies," *Xenotransplantation* 5(1):6-17 (1998).

Cooper, et al., "Manipulation of the anti-alphaGal antibody—alphaGal epitope system in experimental discordant xenotransplantation," *Xenotransplantation* 3: 102-111 (1996).

Cooper, et al., "The pig as potential organ donor for man," *Xenotransplantation* (Cooper, et al., eds.) pp. 481-500 Springer: Heidelberg, 1991.

Cooper, et al., "Extracorporeal immunoadsorption of alpha-Gal antibodies," *Xeno* 4(2): 27-29 (1996).

Cooper, et al., "Effects of cyclosporine and antibody adsorption on pig cardiac xenograft survival in the baboon," *J. Heart Transplant* 7(3):238-246 (1988).

Cooper, et al., "Genetically engineered pigs," *Lancet* 342(8872):682-683 (1993).

Cooper, et al., "Identification of alpha-galactosyl and other carbohydrate epitopes that are bound by human anti-pig antibodies: relevance to discordant xenografting in man," *Transpl Immunol* 1{3}: 198-205 (1993).

Cooper, et al., "Oligosaccharides and discordant xenotransplantation," *Immunol. Rev.* 141:31.58 (1994).

Cozzi, et al., "Effect of transgenic expression of human decay-accelerating factor on the inhibition of hyperacute rejection of pig organs," *Xenotransplantation* (Second edition) (Cooper et al., eds.), pp. 665-682, Springer: Berlin, 1997.

Cozzi, et al., "The generation of transgenic pigs as potential organ donors for humans," *Nature Med* 1(9):964-966 (1995).

Dalmasso, et al., "Inhibition of complement-mediated endothelial cell cytotoxicity by decay-accelerating factor. Potential for prevention of xenograft hyperacute rejection," *Transplantation* 52(3):530-533 (1991).

Dorling, et al., "Clinical xenotransplantation of solid organs," *Lancet* 349(9055):867-871 (1997).

Galili, "The two antibody specificities within human anti-blood group B antibodies," *Transfusion Med. Rev.* 2(2):112-121 (1988).

Galili, et al., "Man, apes, and Old World monkeys differ from other mammals in the expression of alpha-galactosyl epitopes on nucleated cells," *J Biol Chem* 263(33): 17755-17762 (1988).

Galili, et al., "The human natural anti-Gal IgG. III. The subtlety of immune tolerance in man as demonstrated by crossreactivity between natural anti-Gal and anti-B antibodies," *J.Exp. Med.* 165(3):693-704 (1987).

Gentsch and Pacitti, "Effect of neuraminidase treatment of cells and effect of soluble glycoproteins on type 3 reovirus attachment to murine L cells", *J. Virol.*, 56(2):356-64 (1985).

Good, et al., "Identification of carbohydrate structures that bind human antiporcine antibodies: implications for discordant xenografting in humans," *Transplant. Proc.* 24(2):559-562 (1992).

Hansson, "Structural aspects of blood group glycosphingolipids in the gastrointestinal tract," *Adv Exp Med Biol* 228:465-494 (1988).

Hantzopoulos, et al., "Improved gene expression upon transfer of the adenosine deaminase minigene outside the transcriptional unit of a retroviral vector," *Proc. Natl. Acad. Sci. USA* 86(10):3519-3523 (1989).

Hinchliffe, et al., "Molecular cloning and functional characterization of the pig analogue of CD59: relevance to xenotransplantation," *J Immunol* 160(8): 3924-3932 (1998).

Holgersson, et al., "Structural characterization of non-acid glycosphingolipids in kidneys of single blood group O and A pigs," *J Biochem* (Tokyo) 108: 766-777 (1990).

Hughes, et al., "Factors involved in the cytotoxicity of normal guinea pig serum for cells of murine tumor TA3 sublines treated with neuraminidase", *J. Immunol.*, 111(4):1071-80 (1973).

Irie, et al., "CMP-N-Acetylneuraminic acid hydroxylase is exclusively inactive in humans," *Biochem. Biophys. Res.Commun.* 248(2):330-333 (1998).

Joyner, et al., "Production of a mutation in mouse En-2 gene by homologous recombination in embryonic stem cells," *Nature* 338(6211):153-156 (1989).

Katz, et al., "Structure determination of aquomet porcine hemoglobin at 2.8 A resolution," *J Mol Biol* 244(5):541-553 (1994).

Kaufman, et al., "Xenotransplantation", *Ann. Rev. Immunol.*, 13:339-67 (1995).

Kawano, et al., "Molecular cloning of cytidine monophospho-N-acetylneuraminic acid hydroxylase. Regulation of species- and tissue-specific expression of N-glycolylneuraminic acid," *J. Biol. Chem.* 270(27):16458-16463 (1995).

Kirkman, "Of swine and men: Organ physiology in different species," *Xenograft* 25:125-132 (1989).

Kobayashi, et al., "Lack of antibody production against Hanganutziu-Oeicher (H-D) antigens with N-glycolylneuraminic acid in patients with porcine exposure history," *Xenotransplantation* 7(3):177-180 (2000).

Koike, et al, "Introduction of alpha(1,2)-fucosyltransferase and its effect on alpha-Gal epitopes in transgenic pig," *Xenotransplantation* 3:81-86 (1996).

Kujundzic, et al., "Variability of anti-alphagal antibodies in human serum and their relation to serum cytotoxicity against pig cells," *Xenotransplantation* 1:58-65 (1994).

Lai, et al., "Production of alpha-1,3-galactosyltransferase knockout pigs by nuclear transfer cloning," *Science* 295(5557):1089-1092 (2002).

Larsen et al., "Frameshift and nonsense mutations in a human genomic sequence homologous to a murine UDP-Gal:beta-D-Gal(1,4)-D-GlcNAc alpha(1,3)-galactosyltransferase cDNA," *J. Biol. Chem.* 265: 7055-7061 (1990).

Lavecchio, et al., "Enzymatic removal of alpha-galactosyl epitopes from porcine endothelial cells diminishes the cytotoxic effect of natural antibodies," *Transplantation* 60(8):841-847 (1995).

Leibiger, et al, "Structural characterization of the oligosaccharides of a human monoclonal anti-lipopolysaccharide immunoglobulin M," *Glycobiology* 8(5):497-507 (1998).

Lowe et al., "Molecular cloning of a human fucosyltransferase gene that determines expression of the Lewis x and VIM-2 epitopes but not ELAM-1-dependent cell adhesion," *J. Biol. Chem.* 266: 17467-17477 (1991).

Macchiarini, et al., "Evidence of human non-alpha-galactosyl antibodies involved in the hyperacute rejection of pig lungs and their removal by pig organ perfusion, " *J Thorac Cardiovasc Surg* 116(5): 831-843 (1998).

Maclaren, et al., "Variation in porcine red blood cell alpha-galactosyl expression and agglutination by human serum," *Transplant Proc* 30(5):2468 (1998).

Marcus, et al., "Glycosphingolipids with Lewis blood group activity: uptake by human erythrocytes," *Science* 164(879):553-555 (1969).

McMorrow, et al., "Relationship between ABO blood group and levels of Gal alpha,3Galactose-reactive human immunoglobulin G," *Transplantation* 64(3): 546-549 (1997).

Oriol, et al., "Carbohydrate antigens of pig tissues reacting with human natural antibodies as potential targets for hyperacute vascular rejection in pig-to-man organ xenotransplantation," *Transplantation* 56(6):1433-1442 (1993).

Osman, et al, "Combined transgenic expression of alpha-galactosidase and alpha1,2-fucosyltransferase leads to optimal reduction in the major xenoepitope Galalpha(1,3)Gal," *Proc. Natl. Acad. Sci. USA* 94(26):14677-14682 (1997).

Osman, et al, "Switching amino-terminal cytoplasmic domains of alpha(1,2)fucosyltransferase and alpha(1,3)galactosyltransferase alters the expression of H substance and Galalpha(1,3)Gal," *J. Biol. Chem.* 271(51):33105-33109 (1996).

Patience, et al., "Zoonosis in xenotransplantation," *Curr Opin Immunol* 10(5): 539-542 (1998).

Paul, "Mechanism of humoral Xenograft rejection," *Xenotransplantation* (Cooper, et al., eds) pp. 47-67, Springer: Heidelberg, 1991.

Platt, et al., Mechanism of tissue injury in hyperacute Xenograft rejection, *Xenotransplantation: The Transplantation of Organs and Tissues between species*, eds., Springer-Verlag, New York, 69-79 (1991).

Polejaeva, et al., "Cloned pigs produced by nuclear transfer from adult somatic cells," *Nature* 407(6800): 27, 29-30 (2000).

Rao, et al., "Recombinant hemoglobin A produced in transgenic swine: structural equivalence with human hemoglobin A," *Artif Cells Blood Substit Immobil Biotechnol* 22(3): 695-700 (1994).

Romano, et al, "Intravenous synthetic alphaGal saccharides delay hyperacute rejection following pig-to-baboon heart transplantation," *Xenotransplantation* 6(1): 36-42 (1999).

Sako, et al., "Human blood group glycosphingolipids of porcine erythrocytes," *Arch Biochem Biophys* 278(1): 228-237 (1990).

Sandrin, et al., "Anti-pig IgM antibodies in human serum react predominantly with Gal(alpha 1-3)Gal epitopes," *Prot Natl Acad Sci USA* 90(23):11391-11395 (1993).

Sandrin, et al., "Enzymatic remodeling of the carbohydrate surface of a xenogenic cell substantially reduces human antibody binding and complement-mediated cytolysis," *Nat Med* 1(12)1261-1267 (1995).

Sandrin, et al., "Reduction of the major porcine xenoantigen Galalpha (1,3)Gal by expression of alpha (1,2) fucosyltransferase," *Xenotransplantation* 3: 134-140 (1996).

Sharma, et al., "Reduction in the level of Gal(alpha1,3)Gal in transgenic mice and pigs by the expression of an alpha(1,2)fucosyltransferase," *Proc. Natl. Acad. Sci. USA* 93(14):7190-7195 (1996).

Shinkel, et al., "Changes in cell surface glycosylation in alpha1,3-galactosyltransferase knockout and alpha1,2-fucosyltransferase transgenic mice," *Transplantation* 64(2):197.204 (1997).

Simon, et al., "Intraveneous infusion of Galalpha1-3Gal oligosaccharides in baboons delays hyperacute rejection of porcine heart xenografts," *Transplantation* 65: 346-353 (1998).

Slomiany, et al., "Structural study of the blood group A active glycolipids of hog gastric mucosa," *J Biol Chem* 249(4):1225-1230 (1974).

Tachi et al., "Variability of cytotoxicity to pig cultured cells and its determinant factor in human sera," *Transplant. Proc.* 30: 71-73 (1998).

Tanemura, et al., "Suppression of the xenoantigen Gal alpha(1,3)Gal by N-acetylglucosaminyltransferase III (GnT-III) in transgenic mice," *Transplant. Proc.* 29(1-2):895-896 (1997).

Taniguchi, et al., "Clinical xenotransplantation: past, present and future," *Ann. R. Coll. Surg. Engl.* 79(1):13-19 (1997).

Thall, et al., "Oocyte Galalpha 1,3 Gal epitopes implicated in sperm adhesion to the zona pellucida glycoprotein ZP3 are not required for fertilization in the mouse," *J. Biol. Chem.* 270: 21437-21440 (1995).

Van Den Berg, et al., "Understanding the immune protection afforded by endogenous complement regulatory molecules," *Graft* 4: 63-65 (2001).

Van Den Berg, et al., "A rapid method for the isolation of analogues of human CD59 by preparative SDS-PAGE: application to pig CD59," *J. Immunol Methods* 179(2): 223-231 (1995).

Xu, et al., "Removal of anti-porcine natural antibodies from human and nonhuman primate plasma in vitro and in vivo by a Galalpha1-3Galbeta1-4betaGlc-X immunoaffinity column," *Transplantation* 65(2):172-179 (1998).

Ye, et al., "Evidence that intravenously administered alpha-galactosyl carbohydrates reduce baboon serum cytotoxicity to pig kidney cells (PK15) and transplanted pig hearts," *Transplantation*. 58(3):330-337 (1994).

Zhu, "Binding of human natural antibodies to nonaiphaGal xenoantigens on porcine erythrocytes," *Transplantation* 69(11):2422-2428 (2000).

Zhu, "Introduction to porcine red blood cells: Implications for xenotransfusion" *Seminars in Hematology* 37(2): 143-149 (2000).

Zhu, "Anti-N-glycolylneuraminic acid antibodies identified in healthy human serum" *Xenotransplantation* 9: 376-381 (2002).

Irie and Suzuki, "The molecular basis for the absence of N-glycolylneuraminic acid in humans", *Tanpakushitsu Kakusan Koso (Protein, Nucleic Acid, Enzyme)*, 43(16 Suppl):2404-9 (1998).

* cited by examiner

```
                        10         20         30         40         50
CHIM           1 MGSIEQTTET LLCLSPVEVA SLKEGINFPR NKSTGKDYIL YKNKSRLRAC    50

60         70         80         90        100
CHIM          51 KNMCKHQGGL FIKDIEDLAG RSVRCTKHNW KLDVSTMKYI NPPESPCQDE   100

110        120        130        140        150
PIG            1 LVVEKDEENG VLLLELNPPN PWDSEPRSPE DLAFGEVQIT YLTHACMDLK    50
CHIM         101 **MN*R L******* *LQ*** E***** ********   150

160        170        180        190        200
PIG           51 LGDKRMVFDP WLIGPAFARG WWLLHEPPSD WLERLSRADL IYISHMHSDH   100
CHIM         151 ********** ********** ********** *****CQ*** *****L****   200

210        220        230        240        250
PIG          101 LSYPTLKKLA ERRPDVPIYV GNTERPVFWN LNQSGVQLTN INVVPFGIWQ   150
CHIM         201 ********** G****I**** ********** ********** **********   250

260        270        280        290        300
PIG          151 QVDKNLRFMI LMDGVHPEMD TCIIVEYKGH KILNTVDCTR PNGGRLPMKV   200
CHIM         251 ********** ********** ********** ********** **********   300

310        320        330        340        350
PIG          201 ALMMSDFAGG ASGFPMTFSG GKFT...... .......... ..........   250
CHIM         301 ********** ********** ****EEWKAQ FIKTERKKLL NYKARLVKNL   350
```

MODIFIED ORGANS AND CELLS FOR XENOTRANSPLANTATION

This is a divisional of U.S. Ser. No. 10/135,919, filed Apr. 29, 2002 entitled "Modified Organs and Cells for Xenotransplantation" by Alex Zhu issued as U.S. Pat. No. 7,166,278; which claims priority to U.S. Provisional Application No. 60/287,684 filed Apr. 30, 2001, U.S. Provisional Application No. 60/300,604 filed Jun. 22, 2001, and U.S. Provisional Application No. 60/333,876 filed Nov. 28, 2001.

BACKGROUND OF THE INVENTION

The present invention is generally in the field of xenotransplantation, and genetic modification of animals to produce tissue, cells or organs less likely to induce rejection following transplantation.

Shortage of Organs for Transplantation

As reviewed by Dorling, A., et al., Clinical xenotransplantation of solid organs. *Lancet* 349:867-871, 1997, clinical transplantation has evolved over the last forty years to the point that organ allografts (i.e., transplants from one animal into another animal of the same species, such as human to human) are a routine treatment option for end-stage kidney, heart, lung, liver and other organ disease. However, there are not enough cadaveric organs to meet the clinical demand. Xenografts (i.e., transplants from one animal into another animal of a different species, such as from a pig into a human) provide a means for keeping end-stage patients alive, either permanently or temporarily until a suitable allograft can be obtained. Ideally, xenografts will be developed using genetic engineering of non-primate species that are suitable for long-term replacement of damaged or diseased organs and subject only to minimal rejection. However, the organs are still useful even if subject to some form of rejection by the new host. Even in the case of allografts, rejection frequently develops and so patients are immunosuppressed using drugs such as cyclosporine and other types of immunosuppressants to prevent rejection of the allograft.

One solution to the problem of organ supply would be the use of organs taken from a suitable animal donor. Although the higher nonhuman primates (apes and Old World monkeys) would provide the closest immunological match for humans, there are several factors that make the routine use of these species as organ donors unlikely. These include (i) inadequate numbers, (ii) difficulty and expense of breeding in large numbers, (iii) inadequate size of sonic organs (e.g., heart) for adult humans, (iv) probability of public concern regarding the use of such species for this purpose, and (v) risk of transfer of serious viral disease.

Attention is, therefore, being directed towards more commonly available mammals that are lower on the phylogenetic scale, in particular, the pig, which has many advantages in this respect, as reported by Kirkman, R. L., In *Xenograft* 25, Amsterdam, Elsevier, 1989. pp. 125-132; and by Cooper, D. K. C., et al. In *Xenotransplantation*. Heidelberg, Springer, 1991. pp. 481-500. These include (i) availability in large numbers, (ii) inexpensive to breed and maintain, (iii) suitable size for the smallest or largest of humans, (iv) availability of pathogen-free (gnotobiotic) animals, (v) considerable similarities of anatomy and physiology with humans, and (vi) ability to genetically engineer.

Shortage of Safe Blood for Transfusion

Eleven million blood transfusions utilizing packed human red blood cells (RBC) are administered in the U.S. each year (National Blood Data Source, 1998). The U.S. blood supply is chronically inadequate. In 2001, it is anticipated that U.S. Blood Banks will obtain about 250,000 units less than optimally required. Officials are forecasting a critical national shortage during the summer months, when regular blood donors go on vacation and college students also leave the major urban centers. Because the nation has a robust and competitive blood collection and distribution system, periodic shortages of blood do not usually result in deaths, but elective surgeries may need to be postponed and other non-critical needs are not met. As donated blood can be stored under normal conditions for only approximately 42 days, and as less than 5% of eligible donors give blood, severe weather conditions, e.g. snowstorms or hurricanes, by reducing access of potential donors to the Blood Center, often lead to the cancellation of elective surgeries.

Not only is human blood a scarce resource, it also comes with a potential risk to the recipient. Despite new viral screening processes, donated human blood is not considered to be 100% safe. It is estimated that the hepatitis C virus is transmitted once in every 100,000 transfusions, and HIV (the AIDS virus) once in every 676,000. This significant incidence of HIV, hepatitis and other viral agents, particularly in some populations, makes it costly and difficult to provide sufficient safe human blood fur purposes of transfusion. More recently, because of concerns over the increasing incidence of new variant Creutzfeldt-Jacob Disease in Europe, eligibility for blood donation has been made more restrictive by the FDA. This may further impact the availability of blood in the USA.

Because of the difficulty and expense of ensuring that human blood is free of any infectious microorganisms, it would be highly desirable to develop a source of RBCs that would be both unlimited in quantity and free of all infectious agents. Pig red blood cells (pRBCs) could fulfill this role.

Although there has been tremendous interest in developing blood substitutes such as perflurochemicals and hemoglobin derivatives, formidable hurdles have been encountered in clinical trials. As reported, an unexpectedly high number of deaths among patients with trauma led to the termination of clinical trials and the withdrawal of two hemoglobin-based formulations from further development (Sloan, E. P., et al., *JAMA*. 1999: 282: 1857-64). The current absence of a suitable alternative to human RBCs increases the potential importance of pRBCs.

Rejection of Xenografts

Survival of pig-to-human (or other primate) organ or cell transplants is currently limited, however, initially by a severe Immoral immune response (hyperacute rejection) that leads to destruction of the graft within minutes or hours, as reviewed by Taniguchi, S. & Cooper, D. K. C. *Ann. R. Coll. Surg. Engl.* 79, 13-19, 1997; and Cooper, D. K. C., et al. *J. Heart Transplant* 7:238-246, 1988, and subsequently by a delayed humoral response (acute humoral xenograft rejection) that is believed also to be mediated largely by the effect of anti-pig antibodies.

Xenotransplants between closely-related species (e.g., chimpanzee-to-human) can usually survive initial period of blood perfusion without damage, as do allotransplants. Subsequently, the foreign antigens of the transplanted organ trigger the recipient's immune response and the rejection process begins. These xenografts, which are rejected clinically rather like allografts, but in an accelerated manner, are termed concordant xenotransplants.) Xenografts between phylogenetically more distant species (e.g., pig-to-human) follow a clinical course quite different from allotransplants and are termed discordant xenotransplants. In discordant xenografted organs, antibody-mediated (vascular) rejection generally occurs within a few minutes or hours of recirculation, with a typical histopathological pattern of endothelial lesions with severe interstitial hemorrhage and edema. This hyperacute rejection is usually irreversible, but can be delayed by removal of the recipient's natural antibodies against the donor tissue. There is now considerable evidence to suggest that this hyperacute rejection is entirely or largely a result of antibody-mediated complement activation through the classical pathway, as reported by Paul, L. C. in *Xenotransplantation* Heidelberg, Springer, 1991. pp. 47-67; and Platt, J. L., Bach, F. H. In *Xenotransplantation,* Heidelberg, Springer, 1991. pp. 69-79. Much attention has been directed towards inhibiting this humoral response, as described by Cooper, D. K. C., et al. *Immunol. Rev.* 141, 31-58 1994; by Cooper, D. K. C. *Xenotransplantation* 3, 102-111, 1996; and by Alwayn, I. P. J., et al. *Xenotransplantation,* 6, 157-168, 1999.

The Gal Antigen-Anti-Gal Antibody Interaction

Studies have shown that there are certain carbohydrate structures present on the surface of mammalian cells, with the exception of Old World monkeys and apes, that elicit an antibody-mediated rejection immediately following implantation of the cells into humans. The antibodies are pre-existing—that is, they are present in the patient's blood prior to implantation of the xenograft—which is why the humoral, or antibody-mediated, response is so intense and immediate. One carbohydrate structure present in pig but not human that elicits an immune response against the pig tissues when transplanted into humans has previously been identified. This is the Gal epitope. Significant levels of IgG, IgM and IgA anti-Gal antibodies are detected in humans. It is known that the lack of Gal epitopes in humans, apes and Old World monkeys is the result of a mutation in the gene for the enzyme, α1,3galactosyltransferase (α1,3GT) (Larsen, R. D., et al. *J. Biol. Chem.* 265, 7055-7061, 1990). Several approaches have been suggested to prevent the hyperacute rejection resulting from binding of human anti-Gal antibodies to pig Gal antigens:

(1) "Knock out" of the gene encoding the enzyme, α1,3GT, required for the production of Gal (Thall, A. D., et al, *J. Biol. Chem.* 270; 21437-40, 1995). To prevent expression of α1,3GT, the gene could be deleted, interrupted, or replaced, either within the coding region or within the regulatory sequences, so that the enzyme is not produced. This is generally accomplished by manipulation of animal embryos followed by implantation of the embryos in a surrogate mother. The embryos can be manipulated directly by injection of genetic material into the embryo by microinjection or by vectors such as retroviral vectors, or indirectly, by manipulation of embryonic stem cells. The latter methodology is particularly useful when the desired end result is to completely prevent expression of a gene for an active enzyme. This approach is currently not possible with regard to the pig as porcine embryonic stem cells have not been isolated, though it is likely to become possible using nuclear transfer technology. The animals would be genetically engineered so that they do not make the Gal epitopes on the surfaces of their cells.

(2) Reduction or suppression of α1,3GT gene expression. In some cases, it may simply be that one wants to decrease expression of Gal. Where, for example, there is a role for Gal that is essential to viability or health of the animal, the optimum results may be achieved by reduction or suppression, rather than by elimination, of gene expression. In these cases, one may want to introduce a gene for an enzyme that can compete for substrate with the α1,3GT and thus reduce the number of Gal epitopes (Cooper, D. K. C., et al. *Lancet* 342, 682-683, 1993). It is possible to reduce the expression of the Gal epitopes on the animal tissues by inserting a gene for an enzyme that competes with α1,3GT for the common substrate. N-acetyllactosamine, thus reducing the immune response following transplantation. The DNA encoding another enzyme for modification of the sugar structures, such as a sialyltransferase or a fucosyltransferase, can be inserted into the embryo where it is incorporated into the animal's chromosomes and expressed to modify or reduce the immunoreactivity of the Gal structures on the cell surfaces. This has been achieved in mice (Osman, N., et al, *Proc. Natl. Acad. Sci. USA.* 94, 14677-14682, 1997; Shinkel, T. A., et al. *Transplantation* 64, 197-, 1997; Tanemura, M., et al. *Transplant. Proc.* 29, 895, 1997) but to date has been only partially successful in pigs (Koike, C., et al, Xenotransplantation 3, 81-86, 1996; Sharma, A., et al. *Proc. Natl. Acad. Sci. USA* 93, 7190-7195, 1996), and has been reviewed by Cooper, D. K. C. *Xenotransplantation* 5, 6-17, 1998.

It is preferable to modify the epitope to a carbohydrate that is present in the human subject so that antibodies against this carbohydrate are not present in the human recipient of the animal organ. If it is modified to any other carbohydrate, then antibodies to this carbohydrate might develop if the carbohydrate is not naturally occurring in the human subject. This may be achieved by genetically engineering the animals which serve as the source of the xenografts to express either a sialyltransferase or furosyltransferase so that nonGal carbohydrate structures (that are also present in humans) are attached to the substrate (which is usually used for the formation of Gal epitopes) to prevent recognition and binding by the naturally occurring anti-Gal antibodies (Osman, N., et al, *J. Biol. Chem.* 271, 33105-13109, 1996; Osman, et al. *Proc. Natl. Acad. Sci. USA,* 94, 14677-14682, 1997; Sandrin, M. S., et al. *Xenotransplantation* 3; 134-140, 1996; Sandrin, M. S., et al. *Nature Med.* 1, 1261-1267, 1995). A human α-1,3 fucosyltransferase has been cloned by Koszdin & Bowen, *Biochem. Biophys. Res. Comm.* 187, 152-157, 1992; and by Lowe, J. B., et al., *J. Biol. Chem,* 266, 17467-17477, 1991.

(3) Insertion of the gene for α-galactosidase that deletes terminal Gal residues, thus reducing Gal expression (Cooper, D. K. C., et al, *Xenotransplantation* 3, 102-111, 1996; Osman, N., et al, *Proc. Natl. Acad. Sci. USA,* 94, 14677-14682, 1997);

(4) Immunoadsorption of anti-Gal antibodies from the primate recipient. Human serum contains anti-pig antibodies, which include anti-Gal IgG, IgM and IgA (Good, A. H., et al, *Transplant. Proc.* 24, 559-562, 1992; Cooper. D. K. C. et al, Transpl. Immunol. 1, 198-205, 1993; Kujundzic, M., et al. *Xenotransplantation.* 1, 58-65, 1994). Anti-Gal antibodies can be removed from human plasma by plasma exchange or adsorbed by passing the plasma through an immunoaffinity column of one or more of the specific Gal structures. The adsorption of such anti-pig antibodies by the specific Gal carbohydrate can prevent the hyperacute rejection that occurs when xenotransplantation is carried out between pig and a nonhuman primate, as reported by Ye, Y., et al. *Transplantation.* 58, 330-337, 1994; by Cooper, D. K. C., et al. *Xeno.* 4, 27-29, 1996; and by Xu, Y., et al. *Transplantation.* 65, 172-179, 1998.

(5) The intravenous administration of one or more Gal carbohydrates (e.g., synthetic Gal oligosaccharides) that would be bound by the endogenous antibodies and thus prevent binding to the xenotransplant (Ye, Y., et al, *Transplantation.* 58, 330-337, 1994; Simon, P., et al. *Transplantation* 65, 172-179, 1998; Romano E., et al, *Xenotransplantation* 6, 36-42, 1999).

There is increasing evidence to suggest that the same approaches (1-5, above) will prevent or delay the development of acute humoral xenograft rejection, which is the rejection response that develops if hyperacute rejection has been prevented or avoided (Alwayn, I. P. J., et al. *Xenotransplantation.* 6, 157-168, 1999; and reviewed in Buhler, L., et al.

*Frontiers in Bioscience* 4, d416-432, 1999, http://www.bioscience.org/1999/v4/d/buhler/fulltext.htm (Pub med identification number 10209058).

Methods to create pigs, as well as other animals, for use as potential organ and tissue donors, have been developed based on this information. Once genetically engineered animals are produced, tissues, including skin, heart, livers, kidneys, lung, pancreas, small bowel, and components thereof are harvested and can be implanted as known by those skilled in the art of transplantation.

However, all of the above approaches, while useful, have yet to prove fully successful or have not completely solved the problems of antibody-mediated xenograft rejection.

It is therefore an object of the present invention to provide a solution to the problem of alleviating immune rejection of xenotransplants, specifically pig into human, where the rejection is initiated by the presence of glycoprotein and/or glycolipid structures on the vascular endothelium of the xenotransplant which are not found in the human.

It is a further object of the present invention to provide genetically engineered cells, tissues and organs that do not express specific sugars (Gal and NeuGc) which may elicit an immune response, including as complement-mediated response, following transplantation of an animal organ, tissues or cells into a human.

It is a still a further object of the present invention to provide a means for providing animal RBCs that can be transfused into humans without adverse reactions.

It is yet another object of the present invention to provide a means for producing therapeutic glycoproteins without specific immunogens (Gal and NeuGc) to prolong the in vivo half-life of these glycoproteins in humans.

SUMMARY OF THE INVENTION

It has been discovered that there are at least two significant antigens present on the cells of animal species such as pigs that elicit an immune or inflammatory response immediately upon implantation into humans or contact with human serum. The first is a Gal epitope, for example, Galα(1→3)Galβ(1→4)GlcNAc (linear B type 2), Galα(1→3)Galβ(1→4)Glc (linear B type 6), Galα(1→3)Gal (B disaccharide), and Galα (α-D-galactose). The second is an N-glycolylneuraminic acid (NeuGc) structure. By eliminating these epitopes, preferably by genetically engineering the animal so that the NeuGc, or the NeuGc and Gal epitopes, are either not produced or their expression is greatly reduced, or by chemical or enzymatic treatment of its cells to remove the epitopes, it is possible to produce organs, tissues and cells suitable for xenotransplantation into humans.

If necessary, cells can be rendered even more compatible by genetically engineering the animal cells to express one or more human complement regulatory proteins, such as decay accelerating factor (DAF), membrane cofactor protein (MCP), or CD59 (as described by Cozzi E & White D J G. *Nature Med* 1: 964-966, 1995; and by Dalmasso A P, et al. *Transplantation* 1991;52: 530-3), or to express an excess of one or more porcine complement regulatory proteins (as reported by van den Berg C W & Morgan B P. *Graft* 4, 63-65, 2001).

Animals or cells can be engineered or treated enzymatically in vitro to remove the Gal epitopes and NeuGc epitopes, and in the most preferred method, to replace the NeuGc epitopes with NeuAc, thereby protecting them from destruction by antibody directed against the carbohydrate epitopes and yet maintaining their structural integrity and viability.

The same result can be achieved by developing, genetically engineered animals, in particular pigs, by nuclear transfer technology or other genetic engineering, that do not express the Gal or NeuGe carbohydrate epitopes.

The same techniques can also be used to treat glycosylated recombinant therapeutic proteins to prevent their early antibody-mediated destruction when administered to humans. The enzymatic treatment of the glycosylated recombinant proteins will prevent both injury from preformed antibody and the development of induced antibody in the human recipient directed against the carbohydrate epitopes (Gal and NeuGc) on the recombinant proteins. Alternatively, these recombinant proteins can be derived from animals that have been genetically engineered not to express Gal or NeuGc.

DETAILED DESCRIPTION OF THE INVENTION

Abbreviations
α1,3GT=α1,3 galactosyltransferase
CMP-NeuAc hydroxylase=cytidine monophospho-N-acetylneuraminic acid hydroxylase
ES cells=embryonic stem cells
Gal=the Galα1→3 Gal epitope
NeuAc=N-acetylneuraminic acid
NeuGc=N-glycotylneuraminic acid The NeuGc Antigen-Anti-NeuGc Antibody Interaction The two most abundant forms of sialic acid (Schauer, R. *Sialic Acids, Chemistry, Metabolism, and Function*. Vienna, Springer, 1982), are N-acetylneuraminic acid (NeuAc), which is ubiquitously present in nature, and N-glycolylneuraminic acid (NeuGc), which is present in most animals with the notable exception of humans and chickens (Gottschalk, A. *Glycoproteins: Their Composition, Structure and Function*. Amsterdam, Elsevier, 1972, Asaoka, H., & Matsuda, H. *J. Vet. Med. Sci.* 56, 375-377, 1994). NeuGc is synthesized in vivo from NeuAc by the addition of a single hydroxyl group by an enzyme called CMP-NeuAc hydroxylase (Shaw, L., Schauer, R. *Biochem J* 263: 355-363, 1989).

The gene encoding the enzyme has been cloned from mouse, chimpanzee and human (Kawano, T., et al. *J. Biol. Chem.* 270, 16458-16463, 1995). While mouse and chimpanzee genes code for a functional enzyme, the human gene has a partial deletion, resulting in a truncated form without enzymatic activity (Irie, A., & Suzuki, A. *Biochem. Biophys. Res. Commun.* 248, 330-331, 1998). It is believed that this is the only example, on the genomic level, where a human gene differs from its chimpanzee counterpart (Brinkman-Van der Linden, E. C., et al. *J. Biol. Chem,* 275: 8633-8640, 2000; Chou, H. H. et al. *Proc. Natl. Acad. Sci. USA.* 95, 11751-11756, 1998).

Until now, it has been commonly believed that humans do not have naturally-existing antibody against the NeuGc antigen (Tachi, Y., et al. *Transplant. Proc.* 30, 71-73, 1998; Kobayashi, T., et al, *Xenotransplantation,* 7, 177-180, 2000), although such antibody may be induced upon exposure to the antigen. Therefore, anti-NeuGc antibody has not been considered to be directly involved in hyperacute rejection of a pig organ or cells following pig-to-human xenotransplantation.

Recently, antibodies against NeuGc (anti-NeuGc antibodies) have been identified and purified from normal human sera. Based on a sensitive assay using flow cytometry, anti-NeuGc antibody was detected in most healthy human subjects tested, although the amount of it in the serum varied considerably. Anti-NeuGc antibody activity can be specifically inhibited by pre-incubation with NeuGc molecules, but not with NeuAc molecules. The identification of naturally-occuring anti-NeuGc antibody in healthy humans and the presence of NeuGc on pig vascular endothelial cells (Bouhours, D., et al. *Glycoconjugate J.* 13, 947-953, 1996) strongly suggests that the antibody may indeed be involved in the hyperacute rejection of a pig organ or cells transplanted into as human. As indirect evidence of this, complement-mediated hemolysis of pRBCs was induced by human anti-nonGal antibodies, which include mainly anti-NeuGc antibodies.

Accordingly, animals engineered to have the same altered glycosylation have utility as potential donors of organs, tissues or cells to humans.

Construction of Genetically-Engineered Animals

Animal Sources

Animals suitable for genetic engineering experiments can be obtained from standard commercial sources. These include animals such as mice and rats for testing of genetic manipulation procedures, as veil as larger animals such as pigs, cows, sheep, goats, and other animals that have been genetically engineered using techniques known to those skilled in the art. These techniques are briefly summarized below based principally on manipulation of mice and rats.

Microinjection Procedures

The procedures for manipulation of the embryo and for microinjection of DNA are described in detail in Hogan et al. Manipulating the mouse embryo. Cold Spring Harbor Laboratory, Cold Spring Harbor, N.Y. (1986), the teachings of which are incorporated herein. These techniques are readily applicable to embryos of other animal species and, although the success rate is lower, it is considered to be a routine practice to those skilled in this art.

Female animals are induced to superovulate using methodology adapted from the standard techniques used with mice, that is, with an injection of pregnant mare serum gonadotrophin (PMSG; Sigma) followed 48 hours later by an injection of human chorionic gonadotrophin (hCG; Sigma). Females are placed with males immediately after hCG injection. Approximately one day after hCG, the mated females are sacrificed and embryos are recovered from excised oviducts and placed in Dulbecco's phosphate buffered saline with 0.5% bovine serum albumin (BSA; Sigma). Surrounding cumulus cells are removed with hyaluronidase (1 mg/ml). Pronuclear embryos are then washed and placed in Earle's balanced salt solution containing 0.5% BSA (EBSS) in a 37.5° C. incubator with a humidified atmosphere at 5% $CO_2$, 95% air until the time of injection.

At the same time as donor females are mated, randomly cycling adult females are mated with vasectomized males to induce a false pregnancy. At the time of embryo transfer, the recipient females are anesthetized and the oviducts are exposed by an incision through the body wall directly over the oviduct. The ovarian bursa is opened and the embryos to be transferred are inserted into the infundibulum. After the transfer, the incision is closed by suturing.

Embryonic Stem (ES) Cell Methods: Nuclear Transfer and Cloning

Methods for the culturing of cells and the subsequent production of genetically engineered animals, the introduction of DNA into cells by a variety of methods such as electroporation, calcium phosphate/DNA precipitation, and direct injection are described in detail in *Teratocarcinomas and Embryonic Stem Cells, a Practical Approach,* ed. E. J. Robertson, (IRL Press, 1987). Cloned pigs have also been produced using an updated nuclear transfer technology as reported by Polejaeva et al. (*Nature.* 407(6800):27, 29-30, 2000). Techniques such as nuclear transfer for embryo reconstruction may be employed wherein diploid donor nuclei are transplanted into enucleated MII oocytes. This technology along with other procedures that aid in the establishment of customized embryonic stem (ES) cell lines that are genetically identical to those of the recipient have been reviewed by Colman, A, and Kind, A. (*Trends Biotechnol* 18(5):192-196, 2000).

Selection of the desired clone of transgene-containing cells is accomplished through one of several means. In cases involving sequence-specific gene integration, a nucleic acid sequence for recombination with the α1,3GT gene or the gene for CMP-NeuAc hydroxylase, or sequences for controlling expression thereof, is co-precipitated with a gene encoding a marker such as neomycin resistance. Transfection is carried out by one of several methods described in detail in Lovell-Badge, in *Teratocarcinomas and Embryonic Stem Cells, a Practical Approach,* ed. E. J. Robertson, (IRL Press, 1987) or in Potter, H. et al. *Proc. Natl. Acad. Sci. USA* 81, 7161, 1984. Calcium phosphate/DNA precipitation, direct injection, and electroporation are the preferred methods. In these procedures, a number of cells, for example, $0.5 \times 10^6$, are plated into tissue culture dishes and transfected with a mixture of the linearized nucleic acid sequence and 1 mg of pSV2neo DNA (Southern, P. J., Berg, P. *J. Mol. Appl. Gen.* 1:327-341, 1982) precipitated in the presence of 50 mg lipofectin in a final volume of 100 µl. The cells are fed with selection medium containing 10% fetal bovine serum in DMEM supplemented with an antibiotic such as G418 (between 200 and 500 µg/ml). Colonies of cells resistant to G418 are isolated using cloning rings and expanded. DNA is extracted from drug resistant clones and Southern blotting experiments using the nucleic acid sequence as a probe are used to identify those clones carrying the desired nucleic acid sequences. In some experiments, PCR methods are used to identify the clones of interest.

DNA molecules introduced into cells can also be integrated into the chromosome through the process of homologous recombination, described by Capecchi, M. R. (*Science,* 244, 1288-1292, 1989). Direct injection results in a high efficiency of integration. Desired clones are identified through PCR of DNA prepared from pools of injected ES cells. Positive cells within the pools are identified by PCR subsequent to cell cloning (Zimmer, A., GEMS, P. *Nature* 338, 150-153, 1989). DNA introduction by electroporation is less efficient and requires a selection step. Methods for positive selection of the recombination event (i.e., neo resistance) and dual positive-negative selection (i.e., neo resistance and ganciclovir resistance) and the subsequent identification of the desired clones by PCR have been described by Joyner, A. L. et al., *Nature* 338, 153-156, 1989; and Capecchi, M. R. *Science* 244, 1288-1292, 1989.

Randomly cycling adult females are paired with vasectomized males. Recipient females are mated such that they will be at 2.5 to 3.5 days post-mating (for mice, or later for larger animals when required for implantation with blastocysts containing ES cells. At the time of embryo transfer, the recipient females are anesthetized. The ovaries are exposed by making an incision in the body wall directly over the oviduct and the ovary and uterus are externalized. A hole is made in the uterine horn with a needle through which the blastocysts are transferred. After the transfer, the ovary and uterus are pushed back into the body and the incision is closed by suturing. This procedure is repeated on the opposite side if additional transfers are to be made.

Identification of Genetically-Engineered Animals.

Samples (1-2 cm of mouse tails) are removed from young animals. For larger animals, blood or other tissue can be used. To test for chimeras in the homologous recombination experiments, i.e., to look, for contributions or the targeted ES cells to the animals, coat color has been used in mice, although blood could be examined in larger animals. DNA is prepared and analyzed by both Southern blot and PCR to detect transgenic founder ($F_0$) animals and their progeny ($F_1$ and $F_2$). Once the genetically-engineered annuals are identified, lines are established by conventional breeding and used as the donors for tissue removal and implantation using standard techniques for implantation into humans.

Modification of the Genomic DNA Encoding CMP-NeuAC Hydroxylase or α1,3GT.

These manipulations are performed by insertion of cDNA or genomic DNA into the embryo using microinjection or other techniques known to those skilled in the art such as electroporation. The DNA is selected on the basis of the purpose for which it is intended; to inactivate the gene encoding an enzyme such as the CMP-NeuAc hydroxylase or α1,3GT. The enzyme-encoding gene can be modified by homologous recombination with a DNA for at defective enzyme, such as one containing within the coding sequence an antibiotic marker, which can then be used for selection purposes.

The gene encoding an α1,3GT is described by Larsen, et al., *J. Biol. Chem.* 265(12), 7055-7061, 1990. Production, of alpha-1,3-galactosyltransferase knockout pigs by nuclear transfer cloning is described by Lai et al., : Science 2002 Feb 8;295(5557):1089-92.

Animals expressing CMP-NeuAc hydroxylase can be engineered using the same technique. Cloning of this gene is described below. In the preferred embodiment this enzyme is inactivated in the genetically engineered animal.

Nuclear Transfer

A knockout pig can be produced by the use of nuclear transfer technology (Colman A. *Cloning*. 1: 185-200, 2000; Polejaeva I, et al., *Nature*. 407 (6800), 27, 29-30, 2000). A targeted disruption of the α1.3GT gene in porcine cells has been carried out (Polejaeva I. et al., *Nature*, 407 (6800) 27, 29-30, 2000). The approach requires the knockout of the gene for α1,3GT in a single adult, fetal or embryonic cell, e.g., a fibroblast, and nuclear transfer of this modified cell using state-of-the-art techiques. This will result in the birth of a pig heterozygous for α1,3GT gene. Breeding between two such pigs will result in a pig homozygous for Gal knockout. Alternatively, the remaining α1,3GT gene could be knockoed out in the cell before nuclear transfer. The same approach could be used to knockout the gene for CMP-NeuAc hydroxylase.

Double Knockout

A preferred solution to the provision of pRBCs, cells, tissues and organs that are not targets for human natural antibodies would be the breeding of pigs that express neither Gal nor NeuGc epitopes (double-knockout pigs). The crossbreeding of an α1,3GT-knockout pig with a CMP-NeuAc hydroxylase-knockout pig will produce a double-knockout pig. The RBCs or any other cells or organs from the double-knockout pig will be deprived of the two major antigens against which humans have natural xenoreactive antibodies. Gal and NeuGc (and can therefore be characterized by such phenotype). In the case of a double-knockout pig, there would be no need to add NeuAc epitopes, as is necessary in enzyme-treated pRBCs, as synthesis of NeuAc would not be disrupted by the mutation of the CMP-NeuAc hydroxylase gene.

Introduction of Genes Encoding Complement Inhibitors.

The absence of target antigens on pig organs, tissues, cells or pRBCs should negate the need for other genetic manipulations of the pig, such as the creation of a pig transgenic for a human (or additional pig) complement regulatory protein. However, should it be found advantageous, transgenic or nuclear transfer techniques will allow this additional protection of the pRBCs.

Specific membrane proteins which exhibit potent inhibitory activity for the complement cascade have been isolated and molecularly cloned. Protection against the pore-forming activity of the C5B-9 complex can be conferred on non-primate cells by transfection of such cells with a cDNA encoding the human complement, regulatory protein CD59. This protein operates by limiting the incorporation of C9 into the membrane complex C5b-9, as reported by Zhao, J., et al., J. Biol. Chem, 266:13418-13422, 1991; Rollins, S. A., Sims, Pi, J. Immunol. 144:3478-3483, 1990; and Rollins, S. A., et al., *J. Immunol.* 146:2345-2351, 1991.

Other complement inhibitors which have been identified and can be used alone or in combination with CD59 include:

(1) CD46, also known as membrane cofactor protein (MCP), as described by Purcell, D. F. et al., *J. Immunol.* 70:155-161, 1990; Lublin, D. M., et al. *J. Exp. Med.* 168, 181-194, 1988; and Seya, T. & Atkinson, J. P. *Biochem. J.* 264:581-588, 1989. This inhibitor functions by binding to complement component C3b thereby activating molecules that cleave C3b into inactive fragments preventing accumulation of C3b and, therefore, its contribution to the formation of the membrane attack complex (MAC). (See also White, D. J. G. et al, Transpl. Int. 5, 648-?, 1992.)

(2) CD55, also known as decay accelerating factor (DAF) (described by Nicholson-Weller, A., et al., *J. Immunol.* 129: 184-1.89, 1982; Lublin, D. M. & Atkinson, J. P. Annu. Rev. Immunol. 7:35-58, 1989; Medof, M. E. & Atkinson, J. P. *J. Exp. Med.* 165:1731-1736, 1987; and Medof, M. R. et al., *Proc. Natl. Acad. Sci. USA* 84:2007-2011, 1987). This inhibitor is a membrane-bound protein of approximately 70 kD in molecular mass which interferes with the assembly of C3 convertase. See also White, D. I. G. and colleagues reporting that recombinant human DAF provides protection of non-primate cells and organs from lysis by human complement (Cozzi, E. et al. in *Xenotransplantation* (Second edition). Heidelberg, Springer, 1997, pp. 665-62).

Cells suitable fir transplantation into a foreign host are protected from complement-mediated lysis by introducing into the cell DNA encoding a protein, or combination of proteins, inhibiting complement-mediated lysis, for example, CD59, CD55, CD46 and/or other inhibitors of C8 or C9 or certain other proteins in the complement cascade. The DNA is introduced into the cells by transfection or infection with a vector encoding the complement-regulatory protein, and expressed on the surface of the transfected/infected cells. The inhibitor is preferably of the same species of origin as the host into which the cells are to be transplanted.

The gene encoding the complement regulatory protein (inhibitor) can be introduced into a cell of a different species of origin (Cozzi, E., et al. In Cooper, D. K. C. Kemp, E., Platt, J. L., White, D. J. G. *Xenotransplantation* (Second edition). Heidelberg, Springer, 1997, pp. 665-682; and Dalmasso A. P., et al. Transplantation 52: 530-533, 1991), for example, a human CD59 gene can be introduced into a porcine cell so that the cell resists attack when transplanted into a human, or the gene can be introduced into a cell of the same species of origin so that increased amounts of the protein are expressed on the surface of the cell (Van den Berg C. W., Morgan B. P. *Graft* 4, 63-65, 2001). For example, the gene can be placed under the control of a promoter enhancing expression of the gene which is then inserted by homologous recombination into the host cell chromosome at the site where the gene is normally located, but under the control of the promoter which enhances expression, or can be inserted into the chromosome at another locus on the chromosome.

DNA sequence information for CD46, CD55 and CD59 has been reported in the literature. The sequence for CD46 was reported by Lublin, D. M., et al., *J. Exp. Med.* 168:181-194, 1988 (HUMCD46 cDNA Sequence Aquired from GenBank: HUMCD46Q). The sequence reported by Medof, M. E. et al, 1987, for CD55 is reported in GenBank as HUMDAF; HUMDAFC1. The amino acid and nucleic acid sequences encoding CD59 were reported by Philbrick, W. M., et al., *Eur. J. Immunol.* 20, 87-92, 1990.

DNA encoding the complement inhibitors can be introduced into cells in culture using transfection or into embryos for production of transgenic animals expressing the complement inhibitors on the surface of their cells. As known in the art, transfection can be accomplished by electroporation, calcium phosphate precipitation, a lipofectin-based procedure, or microinjection or through use of a "gene gun". In each case, cDNA for the inhibitory protein, such as CD59, is subcloned into a plasmid-based vector which encodes elements for efficient expression in the genetically-engineered cell. The plasmid-based vector preferably contains a marker such as the neomycin gene for selection of stable transfectants with the cytotoxic aminoglyroside G418 in eukaryotic cells and an ampicillin gene for plasmid selection in bacteria. Infection is accomplished by incorporating the genetic sequence for the inhibitory protein into a retroviral vector. Various procedures are known in the art for such incorporation. One such procedure which has been widely used in the art employs a defective murine retrovirus, Psi-2 cells for packaging the retrovirus, and the amphotropic packaging cell line Psi-AM to prepare infectious amphotropic virus for use in infecting the target donor cells, as described by Kohn, D. B., et al., *Blood Cells* 13:285-298, 1987. Alternatively, rather than a detective Moloney murine retrovirus, a retrovirus of the self-inactivating and double-copy type can be used, such as that described by Hantzopoulos, P. A., et al., *Proc. Natl. Acad. Sci. USA* 863519-3523, 1989.

Enzymatic Modification of Xenoantigens on Cells

The Gal epitopes on cells such as porcine RBCs can be readily removed by treatment with α-galactosidase, resulting in RBCs that are no longer reactive with human natural anti-Gal antibody. The other major carbohydrate xenoantigen on pRBCs, the NeuGc epitope, can also be removed from the surface of pRBCs in vitro by the enzyme, neuraminidase. However, this enzyme also removes NeuAc, which may lead to a reduction in the half-life of the cells, if transfused into humans in vivo. This problem can be resolved by treating the neuraminidase-treated pRBCs with the enzyme, sialyltransferase, using CMP-NeuAc as a substrate. The resulting pRBCs will thus have NeuAc, but not NeuGc on the cell surface.

Prevention of Sensitization to Other Carbohydrate and Protein Antigens

Due to their phylogenetic distance, proteins on human RBCs are most likely to be antigenically distinctive from their counterparts in pigs, if they exist. Following pRBC transfusion in a human, however, it is possible, even likely, that newly induced antibodies would develop within 10-21 days in the recipient towards protein determinants in the pRBCs. These induced antibodies could be directed towards protein (or carbohydrate) antigens against which there are no preformed natural antibodies. This may not reduce the therapeutic benefit of the pRBCs, but may preclude further transfusion of RBCs from this source. If the circumstances of the transfusion are such that no further pRBC transfusion is anticipated, then no steps to prevent this induced antibody response may be indicated or necessary. If further pRBC transfusion is likely, however, the induced antibody response can be prevented by the concomitant administration of an anti-CD154 mAb, together with daily pharmacologic immunosuppressive therapy, as long as such mAb therapy is continued on an alternate day basis until pRBCs cells are no longer present in the circulation (as reported by Alwayn, I. P. J., et al. *Xenotransplantation*. 6, 157-168, 1999; Buhler, L., et al. *Transplantation*. 69. 2296-2304, 2000); and by Buhler, L., et al. Transplant. Proc. 33, 716, 2001). Induced antibodies directed towards protein antigens developing after pRBC transfusion would be unlikely to target human RBCs, if subsequently transfused. If there were any similarity of protein domains between human RBCs and pRBCs that might lead to crossreactivity, antibodies to pRBCs would be unlikely to have been induced in the first place.

Other Applications for Enzyme Technology

The same technology can be used to treat recombinant therapeutic proteins to make them more compatible with, and acceptable to, the human immune system. Most therapeutic proteins (monoclonal antibodies, enzyme-regulatory proteins, etc) are produced in non-human expression systems (mammalian cell lines and transgenic animals) and, if they are glycosylated, almost certainly express Gal and NeuGc epitopes. For example, analysis of a human anti-lipopolysaccharide IgM produced by a human-mouse heterohybridoma revealed the presence of Gal epitopes and high amounts of NeuGc; the ratio of NeuGc to NeuAc was found to be 98:2 (Leibiger, H., et al, *Glycobiology*, 8, 497-507, 1998). Therefore, due to the presence of the identified natural antibodies to Gal and NeuGc in human recipients, it is conceivable that any recombinant protein carrying either or both of these antigens may be removed from the circulation much more rapidly than if the protein did not express either or both of these antigens. In addition, these carbohydrate antigens can stimulate an induced immune response, which would further limit the glycosylated protein's in vivo half-life and thus significantly reduce its therapeutic effects.

For example, ACTAVASE® (plasminogen activator by Genentech, Inc.) is a recombinant protein used in patients undergoing myocardial infarction or cerebrovascular occlusion. Due to its short half-life (approximately 5 min), a large dose of the drug (approximately 100 mg) is required for therapeutic effect. The protein is produced in a mammalian cell line (Chinese hamster ovary (CHO) cells). The presence of Gal and NeuGc in hamster cells almost certainly provides an explanation for the observed short half-life of the drug. The technology described herein provides a means to increase the in vivo half-life.

Alternatively, the animal that is to provide the source of the cell line or in which the therapeutic protein (e.g., monoclonal antibody) is to be produced would be genetically engineered to be a Gal/NeuGc double knockout to avoid expression of these carbohydrates.

The present invention will be further understood by reference to the following non-limiting examples.

EXAMPLE 1

Preparation of Pig RBCs for Xenotransplantation

Physiology of Pig Red Blood Cells

As in other mammals, the primary site for erythropoiesis in pigs is bone marrow. Serologically, pRBCs share a number of common characteristics with human RBCs (Table 1) (Pond W. G., Houpt K. A. *The Biology of the Pig*. Ithaca: Comstock Pub. Associates, 1978; Jandl J. H. Blood: Textbook of Hematology, Boston: Little, Brown, 1996). The pRBC is a biconcave disk of approximately 4-8 microns in diameter. The hematocrit of pig blood is 35-47%, with a hemoglobin concentration of 6-17 g/100 ml. The half-life of pRBC is approximately 40 days, in comparison to 60 days for human RBCs.

TABLE 1

Comparison of selected paranteters relating to blood between pig and human.

|  | Pig | Human |
| --- | --- | --- |
| Blood volume | 56-95 ml/kg, 10% | 25-45 ml/kg |
| RBC counts | 5.7-6.9 million/ul | 4.2-6.2 million/ul |
| Size (diameter) | 4-8 um | 7.7 um |
| Life span | 86 + 11.5 days | 120 days |
| Blood groups | 15 | 23 |
| Hematocrit | 35-47% | 38% |
| Isotonic | 0.85% NaCl | 0.9% NaCl |
| Hemoglobin | 5.9-17.4 g/100 ml | 12-18 g/100 ml |

Fifteen pig blood group systems have so far been identified. The most important and well-studied is the A-O(H) system, which is closely related to the human ABO system. The A and O antigens on pRBC are passively adsorbed from circulating plasma glycosphingolipids, in a similar mechanism as human Lewis antigens (Marcus, D. M., Cass, L. E. Science 164: 553-555. 1969), pRBC phenotyping is therefore not entirely reliable. Phenotyping of pigs can be achieved by immunohistochemical staining of buccal epithelial cells with an anti-A monoclonal antibody (mAb) (as used in Blood Banks) and an anti-H lectin antibody (Ulex europaeus) (Villarroya, H., et al, Autoimmunity 6: 47-60, 1990). The glycolipids bearing blood group A have been isolated from porcine stomach mucosa (Slomiany, A., et al., *J. Biol. Chem* 249: 1225-1230, 1974), epithelial cells (Backer, A. E. et al. Glycobiology 7: 943-953, 1997) and erythrocytes (Sako, F., et al., *Arch Biochem Biophys* 278: 228-237, 1990). No blood group B antigen has been detected in any porcine cells (Backer, A. E., et al, *Glycobiology* 7: 943-953, 1997; Sako, F., at al. *Arch Biochem Biophys* 278: 228-237, 1990; Holgersson, J., at al. *J. Biochem* (Tokyo) 108: 766-777, 1990; Hansson, B. C. *Adv Exp Med Biol* 228: 465-494, 1988), which is consistent with serological studies.

Among a few of the well-characterized proteins derived from pRBC, porcine hemoglobin not only shares 85% sequence identity with its human counterpart but also demonstrates a similar three-dimensional structure at 2.8 Å resolution (Katz, D. S., et al. *J Mol Biol* 244: 541-553, 1994). Furthermore, human hemoglobin has been expressed in transgenic pigs, with normal post-translational modifications and biological function (Rao, M. J., et al., *Artif Cells Blood Substit Immobil Biotechnol* 22: 695-700,1994). Another cloned protein from pRBC is the complement regulatory protein CD59 (Van Den Berg, C. W., et al., *J. Immunol Methods* 179: 223-231, 1995). Although the protein is only 48% identical to human CD59 at the amino acid level, pig CD59 is capable of regulating human complement activation (Hinchliffe. S. J., et al. *J. Immunol* 160: 3924-3932, 1998).

The transfusion of A-like pRBCs into a human subject would result in cell lysis or agglutination of the pRBCs if the recipient were of blood type O or B (and therefore had preformed anti-A antibodies). Pig herds are available, however, which have been bred to homogeneity for the O-like blood type, and therefore this potential problem can readily be avoided. All pRBCs to be therapeutically transfused into humans would be derived from O-like pigs.

The Problem Related to Gal Antigen Expression in Pigs pRBCs, however, express the Gal epitope against which humans have preformed (natural) antibodies (Galili, U., et al., *J Biol Chem* 263: 17755-17762, 1988; Good, A. H., et al, *Tranplant Proc* 24: 559-562, 1992; Cooper, D. K. C. Clin. Transplantation, 6, 178-183, 1992; Cooper, D. K. C., et al. *Transpl Immunol* 1: 198-205, 1993; MacLaren, L., et al. Transplant Proc 30: 2468, 1998: Sandrin, M. et al., *Proc Natl. Acad Sci USA* 90: 11391-11395, 1993). Transfusion of unmodified pRBCs into unmodified primate recipients would result in antigen-antibody binding, complement activation, and the immediate lysis of the transfused cells. This would have serious health repercussions for the primate recipient. As with ABO blood group-incompatible RBC transfusions in humans, the anticipated outcome can be readily predicted by in vitro hemagglutinating studies.

pRBCs can, however, be treated in vitro with the enzyme α-galactosidase, which removes the terminal Gal sugar molecule from the surface of the cell, rendering the cell no longer susceptible to binding by anti-Gal antibodies (LaVecchio J. A., et al., *Transplantation* 60; 841-847, 1995). Transfusion of pRBCs treated in this way would prevent lysis of the cells from this mechanism. The removal of the Gal epitope from fresh pRBCs by recombinant α-galactosidase was confirmed by the loss of binding with *Griffonia simplicifolia*-1 (specific for terminal Gal residues), in a hemagglutination assay, and with purified anti-Gal antibody, by flow cytometry analysis.

Different amounts of human serum containing natural antibodies as well as complement components were mixed with 40 µl of 5% pRBC (approximately $2 \times 10^7$ cells) in as total volume of 210 µl. After incubating at 37° C. for 1 hour with constant rotation, the remaining intact cells were removed from the reaction by centrifugation. Hemoglobin molecules released from lysed cells were quantitated by measuring the absorbency at 541 nm. Both untreated and α-galactosidase-treated pRBCs were tested in the assay. α-galactosidase treatment of the pRBCs reduced lysis by 10-fold.

The Problem Related to NonGal Antigen Expression in Pigs

However, pRBCs and other tissues have other terminal sugar molecules expressed on their surface (Cooper, D. K. C. Xenotransplantation. 5, 6-17, 1998; Macchiarini, P., et al. *J Thorac Cardiovasc Surg* 116: 831-843, 1998). These may include oligosaccharides that are common to both pig and human, e.g., N-acetyllactosamine and N-acetylneuraminic acid (NeuAc), and therefore against which humans do not have preformed antibodies and would not make induced antibodies (Oriol, R., et al. *Transplantation*. 56: 1433-42, 1993; Cooper, D. K. C., et al., *Immunol Rev* 141, 31-58, 1994).

In contrast, it has been determined that humans do have preformed antibodies against some nonGal antigenic targets (Zhu, A. *Transplantation*. 69: 2422-8, 2000). α-galactosidase-treated pRBCs are recognized by anti-nonGal antibodies, but not by anti-Gal antibodies, whereas untreated pRBCs interact with both typos of antibodies. The percentage of anti-nonGal antibodies in the total xenoreactivity of human serum can be readily determined by flow cytometry analysis using α-galactosidase-treated and untreated pRBCs. As shown in Table 2, anti-nonGal antibody activity was detected in all human serum samples tested, although the percentage activity varied significantly among different healthy volunteers. Higher anti-Gal activity was detected in the sera containing anti-B antibodies (in samples taken from humans with blood groups A and O), supporting the hypothesis that a subset of anti-B cross-reacts with the Gal epitope (Galili, U., et al. *J. Exp. Med.* 165, 693-704, 1987; Galili, U. *Transfusion Med. Rev.* 2, 112-121, 1988; McMorrow, I. M., et al., *Transplantation* 64: 546-549, 1997).

TABLE 2

Human antibody binding (measured by mean fluorescece intensity) to pRBCs before and after treatment of the cells with α-galactosidase which removes the Gal epitopes. The percentage of antibody that bound to nonGal epitopes is indicated.

| Human Volunteer | Blood Type | MFI of treated/untreated pRBCs (percentage of anti-nonGal antibody) | |
|---|---|---|---|
| 1 | A+ | 50/2313 | (2.2%) |
| 2 | B+ | 63/540 | (11.7%) |
| 3 | O+ | 183/846 | (21.6%) |
| 4 | O+ | 29/618 | (0.8%) |
| 5 | O+ | 417/5826 | (7.2%) |
| 6 | A+ | 49/1682 | (2.9%) |
| 7 | AB | 26/57 | (45.6%) |
| 8 | O+ | 26/566 | (4.6%) |
| 9 | AB (pooled) | 27/78 | (34.6%) |

It is worth pointing out that due to its relatively broad specificity (Yagi, F., et al., *Arch. Biochem. Biophys.* 280: 61-67, 1990), the coffee bean α-galactosidase cleaves not only α1,3-linked Gal residues from the Gal epitope but also other terminal α-galactosyl residues with different glycosidic linkages. Thus, if antigens such as $P^k$ (Cairns, T. et al, Transplant. Proc. 28, 795-796, 1996) and Galα1,3Le$^x$ (Bouhours, D., et al., *Glycoconj. J.* 14: 29-38, 1997) were present on pRBCs, treatment of pRBC with α-galactosidase would be most likely to remove terminal Gal residues from these structures also. Therefore, these two carbohydrate structures are not likely to be involved in the interactions between anti-nonGal antibodies and pRBCs.

Other Advantages of pRBCs for Transfusion into Humans

Compared with the transplantation of a pig organ, the therapeutic transfusion of pRBCs possesses a number of unique and favorable features.

First, unlike most tissue cells, mature pRBCs do not contain a nucleus, and therefore do not harbor porcine endogenous retroviruses (PERVs). PERVs are currently perceived to represent a potential risk of infection to the human recipient of a transplanted pig organ (Patience C, et al., *Curr Opin Immunol* 10: 539-42, 1998). Transfer of genetic material, which might include PERVs, to transfusion recipients would therefore be less of a concern.

Second, because pRBCs lack intracellular organelles, enzyme-treatment with α-galactosidase and neuraminidase will permanently remove the Gal and Neu-Gc epitopes from the cell surface. In contrast, porcine endothelial cells treated with α-galactosidase are capable of regenerating Gal epitopes on the cell surface within a few hours (LaVecchio, J. A., et al. *Transplantation* 60: 841-847, 1995).

Third, pRBCs have a relatively short half-life in vivo. Thus, if any form of immunosuppressive therapy, e.g. anti-CD 154 mAb therapy, is required for the transfusion of pRBCs, the treatment would only be required temporarily.

Double Digestion of pRBCs with α-Galactosidase and Neuraminidase pRBCs are incubated with 100U of α-galactosidase per ml of pRBCs in PBS, pH6.0, containing polyethlene glycol. After incubating at 37° C. for 4 hours, the cells are extensively washed with PBS. In order to avoid the potential problems associated with polyethlene glycol, a procedure using phosphate citrate buffer, ph 5.5 at 26° C. for the enzyme treatment, has been developed. The pRBCs thus generated are deprived of Gal epitopes and are physiologically viable.

The α-galactosidase-treated pRBCs are further digested with neuraminidase (1-2 units per ml of RBCs). After incubating for 2 hrs at 37° C. with gentle rotation, pRBCs are then washed four times with PBS buffer.

The enzyme treatment of pRBCs can be monitored by flow cytometry analysis using purified anti-Gal and anti-NeuGc antibodies. After double digestion with both exoglycosidases, the resultant pRBCs are essentially non-reactive with either of the two preformed xenoreactive antibodies (anti-Gal and anti-NeuGc) present in human blood.

EXAMPLE 2

Masking Neuraminidase-treated pRBCs with NeuAc

Since the treatment of pRBCs with neuraminidase removes not only NeuGc but also NeuAc from the cell surface, the asialyl-RBCs are likely to be unstable in vivo primarily due to the loss of negatively-charged residues from the cell surface and exposure of underlying carbohydrate structures. This obstacle can be overcome by treating with sialyltransferase, using CMP-NeuAc as substrate. There are several well-established procedures for the sialyltransferase reaction described in the literature (Kojima N, et al., *Biochemistry*, 17;33:5772-6, 1994).

EXAMPLE 3

Determination of Relative Importance of Gal and NonGal epitopes on pRBCs

The relative importance of Gal and annual in the destruction of pRBCs by the human immune response has been determined. Following a blood transfusion, mismatched human RBCs, e.g. ABO-incompatible cells, undergo intravascular destruction by the same mechanism as the complement-induced hemolysis observed in vitro. To shed light on how the binding of human xenoreactive antibodies to pRBCs triggers the complement cascade and leads to hemolysis, an in vitro complement assay was established. Different amounts of human serum (containing preformed natural antibodies as well as complement) were mixed with 40 μl of 5% pRBCs (approximately $2 \times 10^7$ cells) in a total volume of 210 μl. After incubating at 37° C. for 1 hour with constant rotation, the remaining intact pRBCs were removed from the reaction by centrifugation. The amount of hemoglobin, released from lysed cells was measured by the absorbency at 541 nm. The amount of serum required to induce 50% of hemolysis ($L_{50}$) was determined to be approximately 9-10 µl under these conditions.

Taking advantage of the fact that α-galactosidase-treated pRBCs are recognized by anti-nonGal antibodies, but not by anti-Gal antibodies, it was possible to assess the effect of anti-nonGal antibodies on complement-mediated hemolysis by using enzyme-treated pRBCs in the assay. α-galactosidase-treated pRBCs underwent serum dosage-dependent hemolysis similar to the untreated pRBCs (above), although substantially more serum was required to achieve the same effect. The $L_{50}$ value for the enzyme-treated pRBCs was 60-70 µl (in contrast to that of the untreated cells of 9-10 µl). Therefore, the data suggest that although anti-Gal antibodies in human serum account for the majority of complement-mediated hemolysis of pRBCs, anti-nonGal antibodies contribute significantly to this process. Although treatment of pRBCs with α-galactosidase removes the Gal epitope and reduces agglutination and lysis by human serum, enzyme-treated cells still cause such a strong agglutination and hemolysis, as indicated by these experiments, that they would be undoubtedly eliminated from the circulation rapidly if transfused, confirming the importance the importance of human anti-nonGal antibodies in xenotransplantation.

EXAMPLE 4

Identification of NeuGc as the Major NonGal Target on pRBCs

N-glycolylneuraminic acid (NeuGc) and N-acetyl-neuraminic acid (NeuAc) are two of the most abundant forms of sialic acid identified in glycoconjugates (Schauer, R. *Sialic Acids, Chemistry, Metabolism, and Function.* Wien: Springer, 1982). NeuGc is present in most animals, with the notable exception of humans and chickens (Asaoka, H., & Matsuda, H. *J Vet Med Sci* 56: 375-377, 1994). The presence of NeuGc epitopes on pig vascular endothelium was identified by Bouhours, D., et al., *Glycoconj J* 13: 947-953, 1996, but its presence on pRBCs was only confirmed recently. However, the literature states that humans rarely have preformed antibodies directed towards these epitopes (Tachi, Y., et al., *Transplant Proc* 30: 71-73, 1998; Kobayashi, T., et al. *Xenotransplantation,* 7, 177-130, 2000) and NeuGc was therefore not thought to be involved in the hyperacute rejection commonly observed following pig-to-primate organ transplantation.

In order to identify the nature of the xenoantigen(s) on pRBCs recognized by human anti-nonGal antibodies, the binding of anti-nonGal antibodies purified from pooled human sera to pRBCs was examined by flow cytometry analysis in the presence of various inhibitors. The data suggest that the monosaccharide NeuGc, but not NeuAc, inhibits approximately 80% of the antibody binding, suggesting that anti-NeuGc antibody is the major componenet of anti-nonGal antibody in most healthy human subjects. Furthermore, combining the data from the complement-mediated hemolysis, the experimental results suggest that human anti-NeuGc antibody is also largely responsible for the complement-mediated hemolysis of α-galactosidase-treated pRBCs. In other words, the presence of NeuGc on pRBCs would lead to rapid lysis of these cells if transfused into humans.

EXAMPLE 5

Digestion of Glycoproteins with α-galactosidase and Neuramindase

The total cell membrane proteins, which carry significant numbers of Gal and NeuGc epitopes, were isolated from pRBCs according to the published procedure (Zhu. A. *Transplantation.* 69, 2422-2428, 2000). The membrane proteins were digested with α-galactosidase and neuraminidase under similar conditions to those described above. The pre- and post-digestion protein samples were analyzed by immunoblotting using purified anti-Gal and anti-NeuGc as primary antibodies.

Under these conditions, it was possible to essentially eliminate all Gal and NeuGc epitopes from the pRBC membrane proteins. The same procedure can be used for removal of any other glycoproteins for the same purpose from other mammalian cells or recombinant therapeutic proteins.

EXAMPLE 6

Cloning of Porcine Acne Encoding CMP-NeuAc Hydroxylase

Figure 1:
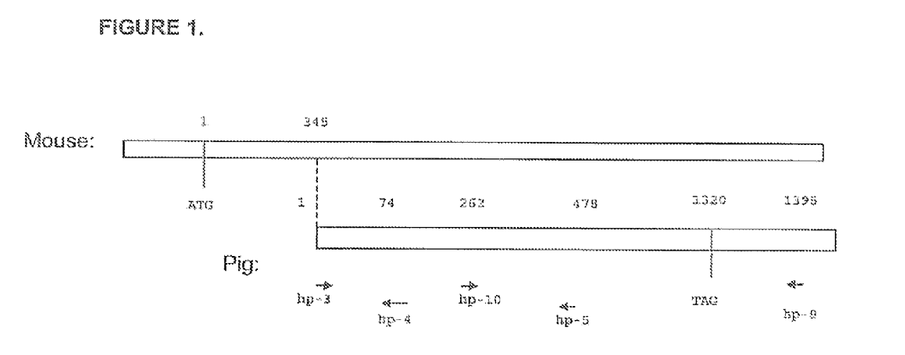
FIG. 1 is a schematic comparison of CMP-NeuAc hydroxylase cDNA from mouse (full length) and pig (partial sequence).

Total RNA was isolated from freshly frozen pig bone marrow according to a standard procedure. The cDNA was then reverse-transcribed from the total RNA using a random primer, followed by PCR amplification using specific primers, hp-3 and hp-9 (FIG. 1). An agarose gel analysis of the PCR product revealed a DNA fragment of approximately 1.4 kb. The fragment was isolated and subcloned into a PCR vector. Sequencing of the insert confirmed that the 1.4 kb fragment was the 3'-end of the cDNA encoding procine CMP-NeuAc hydroxylase.

This 1.4 kb DNA fragment was radioactively labeled as a probe for screening a pig genomic library. After screening over one million plaques, more than ten possible 'positives' were selected using a duplicate-hybridization technique. After the second round of screening under identical conditions, three individual plaques were identified (#41, 46 and 52).

Figure 2:
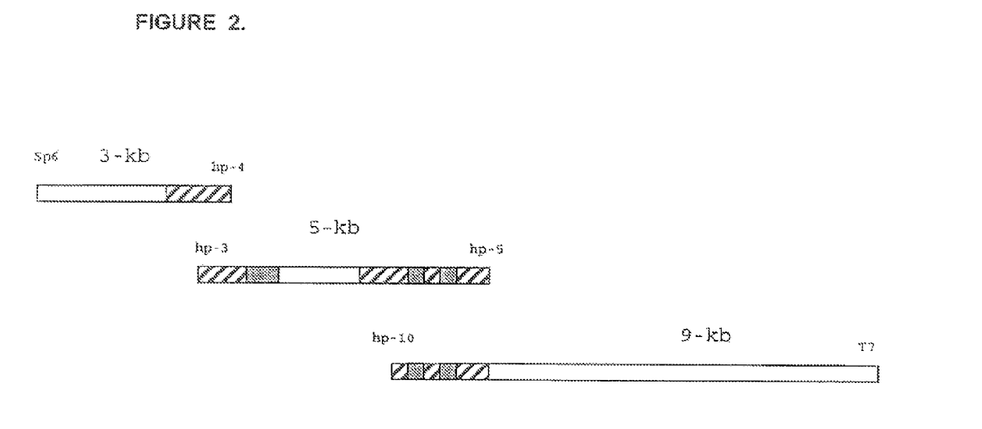
FIG. 2 is a schematic of the partial sequence and gene structure for porcine CMP-NeuAc hydroxylase. The three DNA fragments were amplified using the long PCR procedure from lambda DNA #46. The grey areas are introns and the slashed areas are known sequences. Three overlapped fragments, 3 kb. 5 kb, and 9 kb, were obtained using both universal primers (SP6 and T7) and specific primers. Based on the sequence data, there are at least three introns in the coding regions.

To confirm the authenticity of these three lambda clones, lambda DNA was prepared and restriction digested for as Southern blot. The probe for the Southern blot was the same as the one used for screening the library. All three clones generated DNA fragments strongly hybridized with the probe. Multiple bands on the Southern blot usually result from the internal restriction site of the fragment recognized by the probe. In order to sequence the lambda DNA (#46), different regions of the DNA were amplified using the long PCR procedure of Epicentre Technologies (Madison, Wis.). As shown in FIG. 2, three overlapped fragments, 3 kb, 5 kb, and 9 kb, were obtained using both universal primers (SP6 and T7) and specific primers.

Based on the sequence data, there are at least three introns in the coding regions as indicated by the gray areas in FIG. 2.

Figure 3:
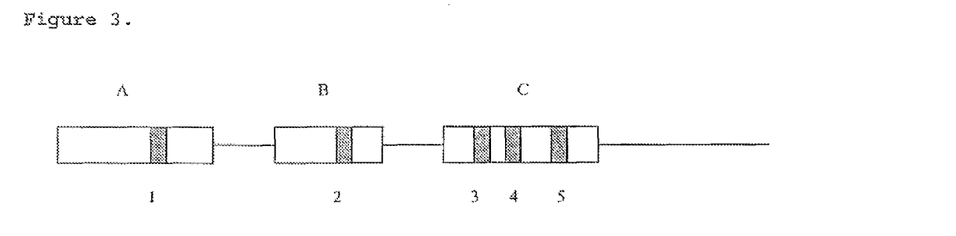
FIG. 3 is a schematic of the sequenced regions and gene structure for porcine CMP-NeuAc hydroxylase. Region A (1614 bp), Region B (1268 bp), and Region C (2763 bp) sequences are shown in SEQ ID NO:1, SEQ ID NO:2, and SEQ NO:3, respectively. The single line represents unsequenced regions. Shaded areas, 1 through 5, represent exons with a total of 224 residues. The sequences corresponding to the shaded areas, 1 through 5, are shown in SEQ ID NO:4, SEQ ID NO:5, SEQ ID NO:6, SEQ ID NO:7, and SEQ ID NO:8, respectively.
Figure 4:
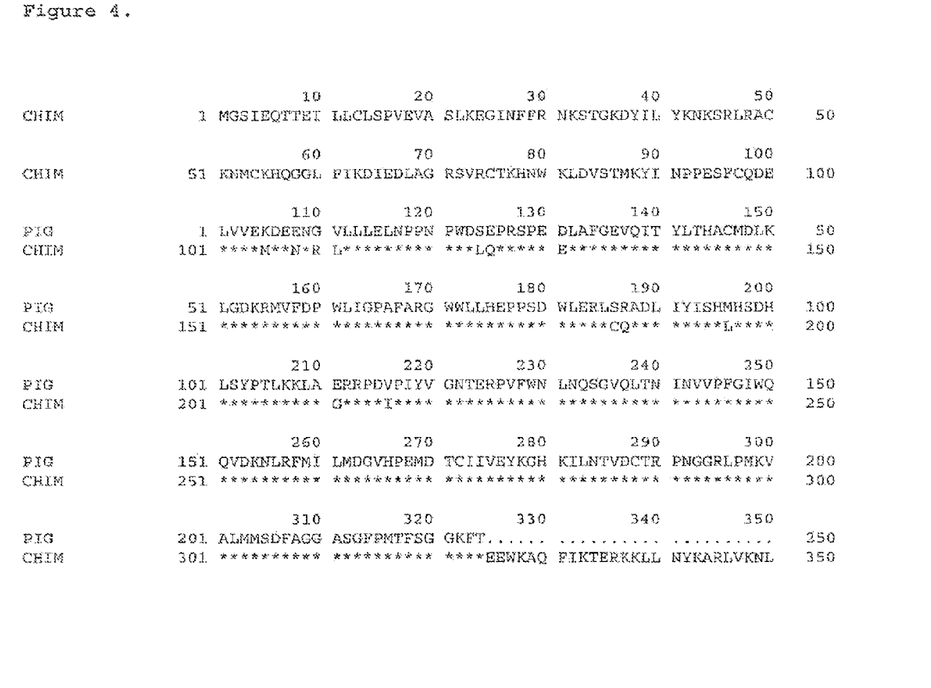
FIG. 4 is an amino acid sequence comparison between pig and chimpanzee CMP-NeuAc Hydroxylase. The pig CMP-NeuAc hydrozylase (SEQ ID NOs:4-8 combined) is compared with the chimpanzee enzyme (SEQ ID NO:9).

The sequence data is illustrated in FIG. 3, wherein the shaded areas represent exons, totaling 224 residues. Shaded areas 1 through 5 are represented by SEQ ID NO:4, SEQ ID NO:5, SEQ ID NO:6, SEQ ID NO:7, and SEQ ID NO:8, respectively. The exons (SEQ ID NO:4 through SEQ ID NO:8) have been combined to generate the comparison shown in FIG. 4, wherein the porcine CMP-NeuAc hydrozylase is compared to the chimpanzee enzyme (SEQ ID NO:9) at the amino acid level. The sequenced nucleotide regions of the porcine CMP-NeuAc hydrozylase, A-C, correspond to SEQ ID NO:1, SEQ ID NO:2, and SEQ ID NO:3, respectively. The rest of the sequencing is routine.

Modifications and variations of the present invention, a method to produce cells, tissues and organs for transplantation, will be obvious to those skilled in the art from the foregoing detailed description. Such modifications and variations are intended to come within the scope of the following claims.

I claim:

1. A method for making porcine organs, tissue or cells less likely to be subject to hyperacute rejection following transplantation into a human comprising
   genetically engineering a pig from which the porcine organs, tissue or cells are derived, to prevent expression of cytidine monophospho-N-acetylneuraminic acid (CMP-N-NeuAc) hydroxylase,
   wherein the pig is also genetically modified to remove or reduce Gal epitopes and to express one or more human complement regulatory proteins.

2. The method of claim 1 wherein the porcine organs, tissue or cells comprise N-acetylneuraminic acid epitopes.

3. The method of claim 1 wherein the porcine cells, tissues or organs have an inactive gene encoding CMP-N-acetylneuraminic acid hydroxylase.

4. The method of claim 1 wherein the porcine organs, tissue, or cells are selected from the group consisting of skin, heart, livers, kidneys, lung, pancreas, small bowel, and components thereof.

5. The method of claim 1 wherein the cells are red blood cells.

6. Porcine organs, tissue or cells less likely to be subject to hyperacute rejection following transplantation into a human produced by a method for making porcine organs, tissue or cells comprising genetically engineering a pig from which the porcine organ, tissue or cells are derived, to prevent expression of cytidine monophospho-N-acetylneuraminic acid (CMP-N-NeuAc) hydroxylase,
   wherein the pig is also genetically modified to remove or reduce Gal epitopes and to express one or more human complement regulatory proteins.

7. The porcine organs, tissues or cells of claim 6 wherein the porcine cells, tissues or organs have an inactive gene encoding CMP-N-acetylneuraminic acid hydroxylase.

8. The porcine organs, tissues or cells of claim 6 comprising N-acetylneuraminic acid epitopes.

9. The porcine organs, tissues or cells of claim 6 wherein the cells are red blood cells.

10. The porcine organs, tissues or cells of claim 6 wherein the porcine organs, tissue, or cells are selected from the group consisting of skin, heart, livers, kidneys, lung, pancreas, small bowel, and components thereof.

* * * * *

SEQUENCE LISTING

```
<160> NUMBER OF SEQ ID NOS: 9

<210> SEQ ID NO 1
<211> LENGTH: 1614
<212> TYPE: DNA
<213> ORGANISM: Sus sp.

<400> SEQUENCE: 1
tgtgcctcac agcgggtctt tctaaaatta agttctgatt ttaattctcc cttgctatag      60
cacttaggta ttgctttcag ccagtgcaat agaaaaacca ggcaaaagtt gctcaatcat     120
ataggaggtt gtttttctta gatcccaagc aggtaatcct gggcattatg gttgttctgt     180
gtttatcaag gagccaaatt ccctatcacc tcctgttcta tcctcagtgt ctggctctat     240
tcttcagcat ctcaagatgg cttgtgctcc tccaagcatg gcagtcaaat tccacacaag     300 aggggaaat atgaagggat gaaggggaga cagtgctggc tcttgagtt gtccctcttt      360 gtcgggaaa taaatgtgtt cctgcaagtc ccgtgagact tctgaagtag acgtctgctt       420
acgtctcacc cgccagaact atgtaaactg cacatagtgc taggtctaca tagccactca     480
taactgccag ggggctggga aatctttaaa taggtgtacc atcacacaat taggatgcta     540
atagtaaggg agaaggagag aataggtttt gcgcaagcca ccagcatgcc tgccacaatt     600
gcttaaaatt cttcattgac ccctcattgc cacaggatga aatccagacg cctccttagt     660
tgggaatcta gggtccttca tgacccactc tgacctacct gtctctccca cctggttcag     720
acaccattct ccttggtcat aaaattccag tcatttgtga acatccagct ctcccatgcc     780
tccatgcctt tgcacatgct gttcttttat cttttatgtt gtccttttat cttttatcca     840
aaagagatat cccatcatca catctctttt gtcagccccc aaatactttg tctttcaagt     900
tcagctggag gattacctcc tatttgaaat cagctttgac tcttacaacc aaacaaggtt     960
ttccttccga gacactccca cagcaccttg aactcatctc tatcaatcat tcatttgatt    1020
gtaatgaagt tggtggtggt gtgcctgtgt ctctgacaca tctgcgatct catgagttcc    1080
ttacgtggaa tgtgaatagc gagatgaaca gtattggtct tcagccctca tctctgcaga    1140
tgttgcttga cccaaatgag cgttgccttt tatttttgatt ttgctttgat ttgtctactc    1200
catgtacttg agccatgcat ttctgtctta gcgatgcttt ttaaaagtca tttttttggt    1260
tgattatcca gatttgtcca cctttgcttc tagttgtaga aaaggatgaa gaaaatggag    1320
ttttgcttct agaactaaat cctcctaacc cgtgggattc agaacccaga tctcctgaag    1380
atttggcttt tggggaagtg caggtaagga aatgttaaat tataatattc ttaaaaacac    1440
aaataaagct aacatatcaa tttatatata tatatatata tatatatatt ttttttttta    1500
catcttatat taccttgagt attcttggaa gtggctagtt aggacatata ataaagttat    1560
tctgaagtct ttttttttttt cttttttccak ggggagcagg ggcttgakgg ggat         1614
```

<210> SEQ ID NO 2
<211> LENGTH: 1268
<212> TYPE: DNA
<213> ORGANISM: Sus sp.

<400> SEQUENCE: 2

| | | | | | |
|---|---|---|---|---|---|
| ggccctaaaa | aaaaaaaaaa | aagagagag | agagagaatt | tcctccagag | aaaacacttt | 60 |
| ggtagtttgg | gagaggtaaa | caaccaaaaa | ttaattttc | tggagtattc | gggaagcttg | 120 |
| taaaaatggg | ctcttacttt | tttgaggaga | caaatgggaa | cctacccaga | agaggcacaa | 180 |
| tcacctgcat | ttgatttctt | gacctctccc | taccttcttt | gctggctttt | cacatttgga | 240 |
| tttctgtgac | cttatctctg | ctccttggtg | ttttcatttt | tcctgtggac | gtgccagact | 300 |
| atgggaaggg | agtaaggcgt | tgatttagaa | tcctgtagtc | tctgcctgtc | tctaagtcat | 360 |
| tgttttcac | ccttctcaaa | ggaccttgac | atcctgagtg | agtccgcaag | taatttaggt | 420 |
| gagaaagcct | tagaagccag | tgcagccagg | ctgcatgact | gtgtccaccc | actggaacca | 480 |
| gtcattctta | tacctattca | cagccaccct | accatttaaa | tccccagagg | tctgccataa | 540 |
| catctgtaac | tcccttcct | tgtaaattgt | gttctaaaag | actggtaaca | aaagatattc | 600 |
| tgtggtacag | agcataatta | aataccttgg | agctgatttg | agttgggtaa | atcaactggt | 660 |
| ttgacccta | aaacccacca | tgagcatttc | tgttctaata | agtaatgcc | tgtgctggga | 720 |
| attgtgttct | acggaaatgc | tcctgctgtg | tcttctga | gtcctgtgtc | attgaacatg | 780 |
| cttaggagca | aagtcccc | atgtggcttg | tctgctaacc | agcccagttc | cttttctgg | 840 |
| ctggtaatga | tccgatcatc | tgaatctcac | tgtcttccaa | cagatcacgt | accttactca | 900 |
| cgcctgcatg | gacctcaagc | tgggagacaa | gaggatggtg | ttcgatcctt | ggttaatcgg | 960 |
| tcctgctttt | gcgcgaggat | ggtggttact | acacgagcct | ccatctgatt | ggctggagag | 1020 |
| gctgagccgc | gcagatttaa | tttacatcag | tcacatgcac | tcagaccacc | tgaggtaagg | 1080 |
| aagggtgagc | cctcaactcc | gaagaaaatg | ctgcaataaa | agcactgttg | gttttcagct | 1140 |
| ttttttgtaa | tcactgctca | ttctgaggta | gattcgcttg | ggctgataaa | aagagaacta | 1200 |
| attcagataa | atgcttgcat | ttgcatagcc | tctttttta | aaaacttttt | ttttttttt | 1260 |
| tttttgg | | | | | 1268 |

<210> SEQ ID NO 3
<211> LENGTH: 2763
<212> TYPE: DNA
<213> ORGANISM: Sus sp.

<400> SEQUENCE: 3

| | | | | | |
|---|---|---|---|---|---|
| agatatatgg | ccgagacctt | ttctctcact | gggagggagc | tgcactgagg | aatgagaaaa | 60 |
| aaaaaaaaaa | tcaagatgaa | accagaaacc | tctttggcga | acttctccct | ctgactttct | 120 |
| gttagaacta | ccccttgcac | aaagcagcat | cagtgtggaa | gacggaattt | gcacacctgg | 180 |
| tttgatatac | atgccgtggt | atatgggatg | ttctaacaat | aaagaggact | ctcccaggaa | 240 |
| atcctcctca | ctgttatagt | cagccttgag | gaaagagctc | ttcttttgga | ctctggggag | 300 |
| agtctagttt | ttcagttcct | tgcttctcgg | tcaacgtgtt | ggtgtaagga | tcacactctc | 360 |
| tcttatacta | gattattcta | tttttcacc | tttcaacctg | tatatctttc | tgaccctagt | 420 |
| tacccaacac | tgaagaagct | tgctgagaga | agaccagatg | ttcccattta | tgttggcaac | 480 |
| acggaaagac | ctgtattttg | gaatctgaat | cagagtggcg | tccagttgac | taatatcaat | 540 |
| gtagtgccat | ttggaatatg | gcagcaggtc | tgtgttcttt | ccacatgttt | tgggttatcc | 600 |

-continued

```
tttctgggat aaatttgagg cgagatagaa attttaagac taaagaaaca atggcctact    660
ttttctgtac atggtcctgt gtaaatctct atttgagctg aaataagatg gtcttcctct    720
ccaattatcc atggtatgac tctgatggat aacaaatcca gttctgaaaa aaggggattt    780
cttccagaa gagaggacag tttcttcaaa tattgaatta aaagcaaaat agatgtaaac    840
cgttgttggt tttattgttg aattccaggt agacaaaaat cttcgattca tgatcttgat    900
ggatggcgtt catcctgaga tggacacttg cattattgtg aatacaaag gtattttctt    960
accctcatca gcaatgaaaa ttgctcttgg tagaaaggat aataatagtt atccaaaaca   1020
tcatcctatg ttcatctgtt tcttccctct tcattttcca tagagtacag tatattctat   1080
ctctgtctta ggaaaatgga ctgtcattca tataatctta cagagaatca attagtaatg   1140
tactctatgc cgtgacaggt gcaaaggttt tttttthaagg caacagataa aaatatccta   1200
tatttcacct attgtaattt ccttaaaact gacattattg aataaatgtt ttactttcat   1260
cttgaatatt attatgttat tggaatcata cactttaccc caataatcat cgaaaagaat   1320
tccaaaaggt tgagagagtt gtgttgatct gattactttc ctctgcatcc tttgagctta   1380
acctttgaat atagtttgct aaggaaagta gtctgtttat gatcctggag tggaatcagg   1440
ctaagtgtcc tcattcagaa cccactgaat cagacagaat gaatttattt ccttgaaagt   1500
tcaaaatgtg tcactcaaga gtataaattt tcaaatctta ctctctcttt tccttggatg   1560
tgagcaattc ttcgataatt gaatgaggca gattatatag acttacatgg aagactgttg   1620
gcctgagaat tcaaactatg gtgttcaaga tttcaccttg agtccgatgc cattttgttt   1680
tcccacaggt cataaaatac tcaatacagt ggattgcacc agacccaatg gaggaaggct   1740
gcctatgaag gttgcattaa tgatgagtga ttttgctgga ggagcttcag gctttccaat   1800
gactttcagt ggtggaaaat ttactggtaa ttcttttatat caaaatgatg ccaaggagtt   1860
ggcatggcac tttgctaaat gctgtgtgaa tcaatacaaa gataattagg acatggttct   1920
tcctcacaag aggtgtgcaa tcttattggg aaatcatact tgcaagtcac aaatatagac   1980
taaagtttcc agctgagaat atgctgatgg agcatgaaac actaaggaga ctagggagaa   2040
tctcaggaaa aatcaagaat aatttggatc aaatggattc ctgacataga acatagagct   2100
gatccttacc tgctgagcca cagggaactc ctggacctgt cttccatgg cccctatgga   2160
atgatcaggc ttctcaaagc cagaccctct gggcacaccc cttctgcctg caggtcctct   2220
ggtttgcttt tttagcagag aagggcagga cagttcagct ctcatgatga agagtcagtc   2280
ttacatgcat gcgcctgcct ggatgacaca acagaaccca ggagggctcc ctgtccaaag   2340
tattggcctc ttgcctgttc tctaattaga gttctttctg cacaggtagt gcaataaagt   2400
agaaagagct tggacttcaa cttcaggcag actgagctca gatctcagct cttctgcaca   2460
ctacagacat ttagcaagtc acttcttttg tgaacccttta tttccacatc tggtacctgg   2520
gataatgtag gtaaaatgc tgagacaata agaactggcc acatactatt tccttcctt   2580
tcttttctga gtctaattgg gtaaatactc tggagctgag taacattcta agcttttata   2640
ttctggcaaa tagatgtctc tctagggaaa ttaattatca gcttcaactg ttatccagaa   2700
tattggtgct ctaaccactc aaggacataa tattttaac aaagatctct ctctctctat   2760
ctc                                                                2763
```

<210> SEQ ID NO 4
<211> LENGTH: 37
<212> TYPE: PRT
<213> ORGANISM: Sus sp.

-continued

```
<400> SEQUENCE: 4

Leu Val Val Glu Lys Asp Glu Glu Asn Gly Val Leu Leu Glu Leu
1               5                   10                  15

Asn Pro Pro Asn Pro Trp Asp Ser Glu Pro Arg Ser Pro Glu Asp Leu
            20                  25                  30

Ala Phe Gly Glu Val
        35

<210> SEQ ID NO 5
<211> LENGTH: 64
<212> TYPE: PRT
<213> ORGANISM: Sus sp.

<400> SEQUENCE: 5

Gln Ile Thr Tyr Leu Thr His Ala Cys Met Asp Leu Lys Leu Gly Asp
1               5                   10                  15

Lys Arg Met Val Phe Asp Pro Trp Leu Ile Gly Pro Ala Phe Ala Arg
            20                  25                  30

Gly Trp Trp Leu Leu His Glu Pro Pro Ser Asp Trp Leu Glu Arg Leu
        35                  40                  45

Ser Arg Ala Asp Leu Ile Tyr Ile Ser His Met His Ser Asp His Leu
    50                  55                  60

<210> SEQ ID NO 6
<211> LENGTH: 50
<212> TYPE: PRT
<213> ORGANISM: Sus sp.

<400> SEQUENCE: 6

Ser Tyr Pro Thr Leu Lys Lys Leu Ala Glu Arg Arg Pro Asp Val Pro
1               5                   10                  15

Ile Tyr Val Gly Asn Thr Glu Arg Pro Val Phe Trp Asn Leu Asn Gln
            20                  25                  30

Ser Gly Val Gln Leu Thr Asn Ile Asn Val Val Pro Phe Gly Ile Trp
        35                  40                  45

Gln Gln
    50

<210> SEQ ID NO 7
<211> LENGTH: 28
<212> TYPE: PRT
<213> ORGANISM: Sus sp.

<400> SEQUENCE: 7

Val Asp Lys Asn Leu Arg Phe Met Ile Leu Met Asp Gly Val His Pro
1               5                   10                  15

Glu Met Asp Thr Cys Ile Ile Val Glu Tyr Lys Gly
            20                  25

<210> SEQ ID NO 8
<211> LENGTH: 45
<212> TYPE: PRT
<213> ORGANISM: Sus sp.

<400> SEQUENCE: 8

His Lys Ile Leu Asn Thr Val Asp Cys Thr Arg Pro Asn Gly Gly Arg
1               5                   10                  15

Leu Pro Met Lys Val Ala Leu Met Met Ser Asp Phe Ala Gly Ala
            20                  25                  30

Ser Gly Phe Pro Met Thr Phe Ser Gly Gly Lys Phe Thr
```

```
                35                  40                  45

<210> SEQ ID NO 9
<211> LENGTH: 350
<212> TYPE: PRT
<213> ORGANISM: Pan troglodytes

<400> SEQUENCE: 9

Met Gly Ser Ile Glu Gln Thr Thr Glu Ile Leu Leu Cys Leu Ser Pro
1               5                   10                  15

Val Glu Val Ala Ser Leu Lys Glu Gly Ile Asn Phe Phe Arg Asn Lys
            20                  25                  30

Ser Thr Gly Lys Asp Tyr Ile Leu Tyr Lys Asn Lys Ser Arg Leu Arg
        35                  40                  45

Ala Cys Lys Asn Met Cys Lys His Gln Gly Gly Leu Phe Ile Lys Asp
    50                  55                  60

Ile Glu Asp Leu Ala Gly Arg Ser Val Arg Cys Thr Lys His Asn Trp
65                  70                  75                  80

Lys Leu Asp Val Ser Thr Met Lys Tyr Ile Asn Pro Pro Glu Ser Phe
                85                  90                  95

Cys Gln Asp Glu Leu Val Val Glu Met Asp Glu Asn Asn Arg Leu Leu
            100                 105                 110

Leu Leu Glu Leu Asn Pro Pro Asn Pro Trp Asp Leu Gln Pro Arg Ser
        115                 120                 125

Pro Glu Glu Leu Ala Phe Gly Glu Val Gln Ile Thr Tyr Leu Thr His
    130                 135                 140

Ala Cys Met Asp Leu Lys Leu Gly Asp Lys Arg Met Val Phe Asp Pro
145                 150                 155                 160

Trp Leu Ile Gly Pro Ala Phe Ala Arg Gly Trp Trp Leu Leu His Glu
                165                 170                 175

Pro Pro Ser Asp Trp Leu Glu Arg Leu Cys Gln Ala Asp Leu Ile Tyr
            180                 185                 190

Ile Ser His Leu His Ser Asp His Leu Ser Tyr Pro Thr Leu Lys Lys
        195                 200                 205

Leu Ala Gly Arg Arg Pro Asp Ile Pro Ile Tyr Val Gly Asn Thr Glu
    210                 215                 220

Arg Pro Val Phe Trp Asn Leu Asn Gln Ser Gly Val Gln Leu Thr Asn
225                 230                 235                 240

Ile Asn Val Val Pro Phe Gly Ile Trp Gln Gln Val Asp Lys Asn Leu
                245                 250                 255

Arg Phe Met Ile Leu Met Asp Gly Val His Pro Glu Met Asp Thr Cys
            260                 265                 270

Ile Ile Val Glu Tyr Lys Gly His Lys Ile Leu Asn Thr Val Asp Cys
        275                 280                 285

Thr Arg Pro Asn Gly Gly Arg Leu Pro Met Lys Val Ala Leu Met Met
    290                 295                 300

Ser Asp Phe Ala Gly Gly Ala Ser Gly Phe Pro Met Thr Phe Ser Gly
305                 310                 315                 320

Gly Lys Phe Thr Glu Glu Trp Lys Ala Gln Phe Ile Lys Thr Glu Arg
                325                 330                 335

Lys Lys Leu Leu Asn Tyr Lys Ala Arg Leu Val Lys Asn Leu
            340                 345                 350
```